US011766219B2

(12) United States Patent
Drasler et al.

(10) Patent No.: US 11,766,219 B2
(45) Date of Patent: Sep. 26, 2023

(54) CARDIAC STIMULATION SYSTEM

(71) Applicant: BOSTON SCIENTIFIC SCIMED, INC., Maple Grove, MN (US)

(72) Inventors: William J. Drasler, Minnetonka, MN (US); Michael J. Pikus, Golden Valley, MN (US); Roger Hastings, Naples, FL (US); Scott R. Smith, Chaska, MN (US); Daniel M. Lafontaine, Plymouth, MN (US); Douglas R. Saholt, Mound, MN (US); Graig L. Kveen, Maple Grove, MN (US); Martin R. Willard, Burnsville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 17/485,918

(22) Filed: Sep. 27, 2021

(65) Prior Publication Data

US 2022/0008010 A1 Jan. 13, 2022

Related U.S. Application Data

(63) Continuation of application No. 16/008,562, filed on Jun. 14, 2018, now Pat. No. 11,154,247, which is a
(Continued)

(51) Int. Cl.
*A61B 5/00* (2006.01)
*A61N 1/05* (2006.01)
(Continued)

(52) U.S. Cl.
CPC .......... *A61B 5/6848* (2013.01); *A61B 5/6882* (2013.01); *A61N 1/059* (2013.01);
(Continued)

(58) Field of Classification Search
CPC ............................. A61N 1/3756; A61N 1/059
See application file for complete search history.

(56) References Cited

U.S. PATENT DOCUMENTS 3,057,356 A 10/1962 Greatbatch
3,357,434 A 12/1967 Abell
(Continued)

FOREIGN PATENT DOCUMENTS

EP 758542 A1 2/1997
EP 0904009 A1 3/1999
(Continued)

OTHER PUBLICATIONS

"U.S. Appl. No. 11/511,152, Preliminary Amendment filed Oct. 17, 2006", 3 pgs.
(Continued)

*Primary Examiner* — Rex R Holmes
*Assistant Examiner* — Jennifer L Ghand
(74) *Attorney, Agent, or Firm* — Seager, Tufte & Wickhem LLP

(57) ABSTRACT

Some embodiments of pacing systems employ wireless electrode assemblies to provide pacing therapy. The wireless electrode assemblies may wirelessly receive energy via an inductive coupling so as to provide electrical stimulation to the surrounding heart tissue. In certain embodiments, the wireless electrode assembly may include one or more biased tines that shift from a first position to a second position to secure the wireless electrode assembly into the inner wall of the heart chamber.

11 Claims, 4 Drawing Sheets

Related U.S. Application Data continuation of application No. 14/044,094, filed on Oct. 2, 2013, now Pat. No. 10,022,538, which is a continuation of application No. 11/549,352, filed on Oct. 13, 2006, now abandoned.

(60) Provisional application No. 60/748,964, filed on Dec. 9, 2005.

(51) Int. Cl.
*A61N 1/368* (2006.01)
*A61N 1/372* (2006.01)
*A61N 1/375* (2006.01)
*A61B 5/283* (2021.01)

(52) U.S. Cl.
CPC .......... *A61N 1/0573* (2013.01); *A61B 5/0031* (2013.01); *A61B 5/283* (2021.01); *A61N 1/3684* (2013.01); *A61N 1/36843* (2017.08); *A61N 1/3756* (2013.01); *A61N 1/37205* (2013.01)

(56) References Cited

U.S. PATENT DOCUMENTS

| | | |
|---|---|---|
| 3,596,662 A | 8/1971 | Bolduc |
| 3,667,477 A | 6/1972 | Susset et al. |
| 3,713,449 A | 1/1973 | Mulier |
| 3,727,616 A | 4/1973 | Lenzkes |
| 3,835,864 A | 9/1974 | Rasor et al. |
| 3,902,501 A | 9/1975 | Citron |
| 3,942,535 A | 3/1976 | Schulman |
| 3,943,936 A | 3/1976 | Rasor et al. |
| 4,010,756 A | 3/1977 | Dumont et al. |
| 4,157,720 A | 6/1979 | Greatbatch |
| 4,162,679 A | 7/1979 | Reenstierna |
| 4,198,991 A | 4/1980 | Harris |
| 4,256,115 A | 3/1981 | Bilitch |
| 4,441,210 A | 4/1984 | Hochmair et al. |
| 4,525,774 A | 6/1985 | Kino et al. |
| 4,543,955 A | 10/1985 | Schroeppel |
| 4,641,664 A | 2/1987 | Botvidsson |
| 4,644,957 A | 2/1987 | Ricciardelli et al. |
| 4,681,111 A | 7/1987 | Silvian |
| 4,721,118 A | 1/1988 | Harris |
| 4,830,006 A | 5/1989 | Haluska et al. |
| 4,858,623 A | 8/1989 | Bradshaw et al. |
| 4,860,750 A | 8/1989 | Frey et al. |
| 4,913,164 A | 4/1990 | Greene et al. |
| 4,953,564 A | 9/1990 | Berthelsen |
| 4,987,897 A | 1/1991 | Funke |
| 5,012,806 A | 5/1991 | De Bellis |
| 5,078,736 A | 1/1992 | Behl |
| 5,113,869 A | 5/1992 | Nappholz et al. |
| 5,139,033 A | 8/1992 | Everett et al. |
| 5,143,090 A | 9/1992 | Dutcher et al. |
| 5,170,802 A | 12/1992 | Mehra |
| 5,178,149 A | 1/1993 | Imburgia et al. |
| 5,193,539 A | 3/1993 | Schulman et al. |
| 5,193,540 A | 3/1993 | Schulman et al. |
| 5,234,437 A | 8/1993 | Sepetka |
| 5,243,977 A | 9/1993 | Frabucco et al. |
| 5,246,014 A | 9/1993 | Williams et al. |
| 5,250,071 A | 10/1993 | Palermo |
| 5,255,693 A | 10/1993 | Dutcher et al. |
| 5,261,916 A | 11/1993 | Engelson |
| 5,300,107 A | 4/1994 | Stokes et al. |
| 5,304,195 A | 4/1994 | Twyford et al. |
| 5,312,415 A | 5/1994 | Palermo |
| 5,312,439 A | 5/1994 | Loeb |
| 5,314,458 A | 5/1994 | Najaf et al. |
| 5,324,316 A | 6/1994 | Schulman et al. |
| 5,324,325 A | 6/1994 | Moaddeb |
| 5,335,664 A | 8/1994 | Nagashima |
| 5,336,252 A | 8/1994 | Cohen |
| 5,342,408 A | 8/1994 | Decoriolis et al. |
| 5,350,397 A | 9/1994 | Palermo et al. |
| 5,383,915 A | 1/1995 | Adams |
| 5,383,924 A | 1/1995 | Brehier |
| 5,405,367 A | 4/1995 | Schulman et al. |
| 5,411,535 A | 5/1995 | Fujii et al. |
| 5,411,537 A | 5/1995 | Munshi et al. |
| 5,447,533 A | 9/1995 | Vachon et al. |
| 5,487,760 A | 1/1996 | Villafana |
| 5,531,780 A | 7/1996 | Vachon |
| 5,571,148 A | 11/1996 | Loeb et al. |
| 5,591,217 A | 1/1997 | Barreras |
| 5,622,168 A | 4/1997 | Keusch et al. |
| 5,624,316 A | 4/1997 | Roskowski et al. |
| 5,628,778 A | 5/1997 | Kruse et al. |
| 5,674,259 A | 10/1997 | Gray |
| 5,735,887 A | 4/1998 | Barreras et al. |
| 5,755,764 A | 5/1998 | Schroeppel |
| 5,769,877 A | 6/1998 | Barreras |
| 5,772,693 A | 6/1998 | Brownlee |
| 5,775,331 A | 7/1998 | Raymond et al. |
| 5,779,715 A | 7/1998 | Tu |
| 5,792,208 A | 8/1998 | Gray |
| 5,800,535 A | 9/1998 | Howard, III |
| 5,807,397 A | 9/1998 | Barreras |
| 5,814,089 A | 9/1998 | Stokes et al. |
| 5,833,715 A | 11/1998 | Vachon et al. |
| 5,851,227 A | 12/1998 | Spehr |
| 5,861,019 A | 1/1999 | Sun et al. |
| 5,871,532 A | 2/1999 | Schroeppel |
| 5,876,429 A | 3/1999 | Schroeppel |
| 5,876,431 A | 3/1999 | Spehr et al. |
| 5,954,757 A | 9/1999 | Gray |
| 5,995,876 A | 11/1999 | Kruse et al. |
| 6,006,139 A | 12/1999 | Kruse et al. |
| 6,035,239 A | 3/2000 | Patag et al. |
| 6,041,258 A | 3/2000 | Cigaina et al. |
| 6,044,300 A | 3/2000 | Gray |
| 6,053,873 A | 4/2000 | Govari et al. |
| 6,115,636 A | 9/2000 | Ryan |
| 6,123,724 A | 9/2000 | Denker |
| 6,132,456 A | 10/2000 | Sommer et al. |
| 6,141,588 A | 10/2000 | Cox et al. |
| 6,141,591 A | 10/2000 | Weber et al. |
| 6,144,879 A | 11/2000 | Gray |
| 6,144,880 A | 11/2000 | Ding et al. |
| 6,161,029 A | 12/2000 | Spreigl et al. |
| 6,164,284 A | 12/2000 | Schulman et al. |
| 6,200,303 B1 | 3/2001 | Verrior et al. |
| 6,208,894 B1 | 3/2001 | Schulman et al. |
| 6,223,079 B1 | 4/2001 | Bakels et al. |
| 6,240,316 B1 | 5/2001 | Richmond et al. |
| 6,266,567 B1 | 7/2001 | Ishikawa et al. |
| 6,315,721 B2 | 11/2001 | Schulman et al. |
| 6,317,615 B1 | 11/2001 | KenKnight et al. |
| 6,322,559 B1 | 11/2001 | Daulton et al. |
| 6,336,937 B1 | 1/2002 | Vonesh et al. |
| 6,345,202 B2 | 2/2002 | Richmond et al. |
| 6,351,673 B1 | 2/2002 | Ding et al. |
| 6,360,127 B1 | 3/2002 | Ding et al. |
| 6,363,279 B1 | 3/2002 | Ben-Haim et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,409,674 B1 | 6/2002 | Brockway et al. |
| 6,441,747 B1 | 8/2002 | Khair et al. |
| 6,442,413 B1 | 8/2002 | Silver |
| 6,445,953 B1 | 9/2002 | Bulkes et al. |
| 6,456,256 B1 | 9/2002 | Amundson et al. |
| 6,501,983 B1 | 12/2002 | Natarajan et al. |
| 6,510,345 B1 | 1/2003 | Van Bentem |
| 6,522,926 B1 | 2/2003 | Kieval et al. |
| 6,542,775 B2 | 4/2003 | Ding et al. |
| 6,556,874 B2 | 4/2003 | Audoglio |
| 6,564,807 B1 | 5/2003 | Schulman et al. |
| 6,571,127 B1 | 5/2003 | Ben-Haim et al. |
| 6,574,510 B2 | 6/2003 | Von Arx et al. |
| 6,582,441 B1 | 6/2003 | He et al. |

(56) References Cited

U.S. PATENT DOCUMENTS

| | | |
|---|---|---|
| 6,589,230 B2 | 7/2003 | Gia et al. |
| 6,614,406 B2 | 9/2003 | Amundson et al. |
| 6,647,291 B1 | 11/2003 | Bonner et al. |
| 6,647,292 B1 | 11/2003 | Bardy et al. |
| 6,684,109 B1 | 1/2004 | Osypka |
| 6,783,499 B2 | 8/2004 | Schwartz |
| 6,856,836 B2 | 2/2005 | Ding et al. |
| 6,859,665 B2 | 2/2005 | Ding et al. |
| 6,895,265 B2 | 5/2005 | Silver |
| 6,895,280 B2 | 5/2005 | Meadows et al. |
| 6,897,788 B2 | 5/2005 | Khair et al. |
| 6,901,294 B1 | 5/2005 | Whitehurst et al. |
| 6,907,285 B2 | 6/2005 | Denker et al. |
| 6,917,833 B2 | 7/2005 | Denker et al. |
| 6,947,792 B2 | 9/2005 | Ben-Haim et al. |
| 6,970,742 B2 | 11/2005 | Mann et al. |
| 6,978,173 B2 | 12/2005 | Stoll et al. |
| 7,003,350 B2 | 2/2006 | Denker et al. |
| 7,006,864 B2 | 2/2006 | Echt et al. |
| 7,050,849 B2 | 5/2006 | Echt et al. |
| 7,054,691 B1 | 5/2006 | Kuzma et al. |
| 7,062,318 B2 | 6/2006 | Ben-Haim et al. |
| 7,076,305 B2 | 7/2006 | Imran et al. |
| 7,184,830 B2 | 2/2007 | Echt et al. |
| 7,200,437 B1 | 4/2007 | Nabutovsky et al. |
| 7,209,783 B2 | 4/2007 | Fellows et al. |
| 7,231,260 B2 | 6/2007 | Wallace et al. |
| 7,289,853 B1 | 10/2007 | Campbell et al. |
| 7,410,497 B2 | 8/2008 | Hastings et al. |
| 7,522,962 B1 | 4/2009 | Doron et al. |
| 7,532,932 B2 | 5/2009 | Denker et al. |
| 7,532,933 B2 | 5/2009 | Hastings et al. |
| 7,558,631 B2 | 7/2009 | Cowan et al. |
| 7,565,195 B1 | 7/2009 | Kroll et al. |
| 7,606,621 B2 | 10/2009 | Brisken et al. |
| 7,610,092 B2 | 10/2009 | Cowan et al. |
| 7,615,010 B1 | 11/2009 | Najaf et al. |
| 7,634,313 B1 | 12/2009 | Kroll et al. |
| 7,647,109 B2 | 1/2010 | Hastings et al. |
| 7,650,186 B2 | 1/2010 | Hastings et al. |
| 7,702,392 B2 | 4/2010 | Echt et al. |
| 7,765,001 B2 | 7/2010 | Echt et al. |
| 7,809,438 B2 | 10/2010 | Echt et al. |
| 7,840,281 B2 | 11/2010 | Kveen et al. |
| 7,848,815 B2 | 12/2010 | Brisken et al. |
| 7,848,823 B2 | 12/2010 | Drasler et al. |
| 7,877,136 B1 | 1/2011 | Moffitt et al. |
| 7,877,142 B2 | 1/2011 | Moaddeb et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,904,170 B2 | 3/2011 | Harding |
| 7,937,148 B2 | 5/2011 | Jacobson |
| 7,937,161 B2 | 5/2011 | Hastings et al. |
| 7,945,333 B2 | 5/2011 | Jacobson |
| 7,996,087 B2 | 8/2011 | Cowan et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,050,774 B2 | 11/2011 | Kveen et al. |
| 8,165,694 B2 | 4/2012 | Carbanaru et al. |
| 8,185,213 B2 | 5/2012 | Kveen et al. |
| 8,204,595 B2 | 6/2012 | Pianca et al. |
| 8,204,605 B2 | 6/2012 | Hastings et al. |
| 8,260,416 B2 | 9/2012 | Ben-Haim et al. |
| 8,290,600 B2 | 10/2012 | Hastings et al. |
| 8,332,036 B2 | 12/2012 | Hastings et al. |
| 8,340,780 B2 | 12/2012 | Hastings et al. |
| 8,478,408 B2 | 7/2013 | Hastings et al. |
| 8,644,934 B2 | 2/2014 | Hastings et al. |
| 8,738,147 B2 | 5/2014 | Hastings et al. |
| 9,308,374 B2 | 4/2016 | Kveen et al. |
| 10,022,538 B2 | 7/2018 | Drasler et al. |
| 2001/0018547 A1 | 8/2001 | Mechlenburg et al. |
| 2002/0018379 A1 | 2/2002 | Hakuchoh et al. |
| 2002/0026228 A1 | 2/2002 | Schauerte |
| 2002/0052632 A1 | 5/2002 | Ben-Haim et al. |
| 2002/0065543 A1 | 5/2002 | Gomperz et al. |
| 2002/0077556 A1 | 6/2002 | Schwartz |
| 2002/0077685 A1 | 6/2002 | Sundquist et al. |
| 2002/0123774 A1 | 9/2002 | Loeb et al. |
| 2002/0123785 A1 | 9/2002 | Zhang et al. |
| 2002/0128546 A1 | 9/2002 | Silver |
| 2002/0138009 A1 | 9/2002 | Brockway et al. |
| 2002/0138100 A1 | 9/2002 | Stoll et al. |
| 2002/0183791 A1 | 12/2002 | Denker et al. |
| 2002/0183823 A1 | 12/2002 | Pappu |
| 2002/0188323 A1 | 12/2002 | Penner et al. |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0050685 A1 | 3/2003 | Nikolic et al. |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0074041 A1 | 4/2003 | Parry et al. |
| 2003/0088278 A1 | 5/2003 | Bardy et al. |
| 2003/0109914 A1 | 6/2003 | Westlund et al. |
| 2003/0114735 A1 | 6/2003 | Silver et al. |
| 2003/0114742 A1 | 6/2003 | Lewkowicz et al. |
| 2003/0130571 A1 | 7/2003 | Lattouf |
| 2003/0158584 A1 | 8/2003 | Cates et al. |
| 2003/0181958 A1 | 9/2003 | Dobak, III |
| 2003/0181959 A1 | 9/2003 | Dobak, III |
| 2003/0204206 A1 | 10/2003 | Padua et al. |
| 2003/0216729 A1 | 11/2003 | Marchitto et al. |
| 2003/0236518 A1 | 12/2003 | Marchitto et al. |
| 2004/0019364 A1 | 1/2004 | Kieval et al. |
| 2004/0059280 A1 | 3/2004 | Makower et al. |
| 2004/0059392 A1 | 3/2004 | Parramon et al. |
| 2004/0073267 A1 | 4/2004 | Holzer |
| 2004/0087831 A1 | 5/2004 | Michels et al. |
| 2004/0097805 A1 | 5/2004 | Verard et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0116992 A1 | 6/2004 | Wardle et al. |
| 2004/0127895 A1 | 7/2004 | Flock et al. |
| 2004/0147969 A1 | 7/2004 | Mann et al. |
| 2004/0147973 A1 | 7/2004 | Hauser |
| 2004/0167580 A1 | 8/2004 | Mann et al. |
| 2004/0171355 A1 | 9/2004 | Yu et al. |
| 2004/0172083 A1 | 9/2004 | Penner |
| 2004/0176672 A1 | 9/2004 | Silver et al. |
| 2004/0176822 A1 | 9/2004 | Thompson et al. |
| 2004/0193092 A1 | 9/2004 | Deal |
| 2004/0193229 A1 | 9/2004 | Starkebaum et al. |
| 2004/0210282 A1 | 10/2004 | Flock et al. |
| 2004/0215092 A1 | 10/2004 | Fischell et al. |
| 2004/0215280 A1 | 10/2004 | Dublin et al. |
| 2004/0230090 A1 | 11/2004 | Hegde et al. |
| 2004/0230255 A1 | 11/2004 | Dobak, III |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0051243 A1 | 3/2005 | Forbes Jones et al. |
| 2005/0057905 A1 | 3/2005 | He et al. |
| 2005/0060011 A1 | 3/2005 | Denker et al. |
| 2005/0065575 A1 | 3/2005 | Dobak |
| 2005/0065589 A1 | 3/2005 | Schneider et al. |
| 2005/0080346 A1 | 4/2005 | Gianchandani et al. |
| 2005/0080459 A1 | 4/2005 | Jacobson et al. |
| 2005/0095197 A1 | 5/2005 | Tuszynski et al. |
| 2005/0096702 A1 | 5/2005 | Denker et al. |
| 2005/0131511 A1 | 6/2005 | Westlund |
| 2005/0136385 A1 | 6/2005 | Mann et al. |
| 2005/0149138 A1 | 7/2005 | Min et al. |
| 2005/0165456 A1 | 7/2005 | Mann et al. |
| 2005/0182456 A1 | 8/2005 | Ziobro et al. |

(56) References Cited

U.S. PATENT DOCUMENTS

| | | |
|---|---|---|
| 2005/0182465 A1 | 8/2005 | Ness |
| 2005/0192637 A1 | 9/2005 | Girouard et al. |
| 2005/0215764 A1 | 9/2005 | Tuszynski et al. |
| 2005/0245846 A1 | 11/2005 | Casey |
| 2005/0251238 A1 | 11/2005 | Wallace et al. |
| 2005/0251240 A1 | 11/2005 | Doan |
| 2005/0256549 A1 | 11/2005 | Holzer |
| 2005/0261741 A1 | 11/2005 | Libbus et al. |
| 2005/0273014 A1 | 12/2005 | Gianchandani et al. |
| 2005/0288596 A1 | 12/2005 | Eigler et al. |
| 2005/0288717 A1 | 12/2005 | Sunagawa |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0064135 A1 | 3/2006 | Brockway |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095089 A1 | 5/2006 | Soykan et al. |
| 2006/0136001 A1 | 6/2006 | Ortega et al. |
| 2006/0136004 A1 | 6/2006 | Cowan et al. |
| 2006/0173504 A1 | 8/2006 | Zhu et al. |
| 2006/0173505 A1 | 8/2006 | Salo et al. |
| 2006/0178719 A1 | 8/2006 | Ideker et al. |
| 2006/0206170 A1 | 9/2006 | Denker et al. |
| 2006/0241705 A1 | 10/2006 | Neumann et al. |
| 2006/0247753 A1 | 11/2006 | Wenger et al. |
| 2007/0075905 A1 | 4/2007 | Denker et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088418 A1 | 4/2007 | Jacobson |
| 2007/0106357 A1 | 5/2007 | Denker et al. |
| 2007/0135882 A1 | 6/2007 | Drasler et al. |
| 2007/0135883 A1 | 6/2007 | Drasler et al. |
| 2007/0150009 A1 | 6/2007 | Kveen et al. |
| 2007/0150037 A1 | 6/2007 | Hastings et al. |
| 2007/0150038 A1 | 6/2007 | Hastings et al. |
| 2007/0162079 A1 | 7/2007 | Shemer et al. |
| 2007/0203556 A1 | 8/2007 | Rutten et al. |
| 2007/0219590 A1 | 9/2007 | Hastings et al. |
| 2007/0239248 A1 | 10/2007 | Hastings et al. |
| 2007/0276444 A1 | 11/2007 | Gelbart et al. |
| 2007/0293904 A1 | 12/2007 | Gelbart et al. |
| 2008/0021505 A1 | 1/2008 | Hastings et al. |
| 2008/0021532 A1 | 1/2008 | Kveen et al. |
| 2008/0039904 A1 | 2/2008 | Bulkes et al. |
| 2008/0046040 A1 | 2/2008 | Denker et al. |
| 2008/0077184 A1 | 3/2008 | Denker et al. |
| 2008/0077188 A1 | 3/2008 | Denker et al. |
| 2008/0109054 A1 | 5/2008 | Hastings et al. |
| 2008/0119911 A1 | 5/2008 | Rosero |
| 2008/0140142 A1 | 6/2008 | Darvish et al. |
| 2008/0262588 A1 | 10/2008 | Zarembo et al. |
| 2008/0288039 A1 | 11/2008 | Reddy |
| 2008/0306359 A1 | 12/2008 | Zdeblick et al. |
| 2008/0319502 A1 | 12/2008 | Sunagawa et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0204170 A1 | 8/2009 | Hastings et al. |
| 2009/0234407 A1 | 9/2009 | Hastings et al. |
| 2009/0275998 A1 | 11/2009 | Burnes et al. |
| 2010/0094367 A1 | 4/2010 | Sen |
| 2010/0100144 A1 | 4/2010 | Shuros et al. |
| 2010/0198288 A1 | 8/2010 | Ostroff |
| 2010/0228308 A1 | 9/2010 | Cowan et al. |
| 2010/0286744 A1 | 11/2010 | Echt et al. |
| 2010/0314775 A1 | 12/2010 | Schwarzbauer |
| 2011/0034939 A1 | 2/2011 | Kveen et al. |
| 2011/0071586 A1 | 3/2011 | Jacobson |
| 2011/0077708 A1 | 3/2011 | Ostroff |
| 2011/0190835 A1 | 8/2011 | Brockway et al. |
| 2011/0208260 A1 | 8/2011 | Jacobson |
| 2011/0213233 A1 | 9/2011 | Stevenson et al. |
| 2011/0218587 A1 | 9/2011 | Jacobson |
| 2011/0237967 A1 | 9/2011 | Moore et al. |
| 2011/0251660 A1 | 10/2011 | Griswold |
| 2011/0251662 A1 | 10/2011 | Griswold et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2012/0078322 A1 | 3/2012 | Dal Molin et al. |
| 2012/0089198 A1 | 4/2012 | Ostroff |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0158111 A1 | 6/2012 | Khairkhahan et al. |
| 2012/0172690 A1 | 7/2012 | Anderson et al. |
| 2012/0232565 A1 | 9/2012 | Kveen et al. |
| 2013/0268042 A1 | 10/2013 | Hastings et al. |
| 2014/0012344 A1 | 1/2014 | Hastings et al. |

FOREIGN PATENT DOCUMENTS

| | | |
|---|---|---|
| EP | 1166820 A2 | 1/2002 |
| EP | 1166832 A1 | 1/2002 |
| EP | 1264572 A1 | 12/2002 |
| EP | 1809372 A1 | 7/2007 |
| EP | 1812104 A1 | 8/2007 |
| EP | 1835962 A1 | 9/2007 |
| EP | 1957147 A1 | 8/2008 |
| EP | 1957148 A1 | 8/2008 |
| EP | 1973605 A2 | 10/2008 |
| EP | 2254663 B1 | 8/2012 |
| EP | 2001552 B1 | 9/2012 |
| FR | 2559391 A1 | 8/1985 |
| JP | 61203730 A | 9/1986 |
| JP | 62254770 A | 11/1987 |
| JP | 02307481 A | 12/1990 |
| JP | 6510459 A | 6/1992 |
| JP | 05076501 A | 3/1993 |
| JP | H05245215 A | 9/1993 |
| JP | 7016299 A | 1/1995 |
| JP | 9508054 A | 8/1997 |
| JP | 10509901 A | 9/1998 |
| JP | 2000502931 A | 3/2000 |
| JP | 2001511406 A | 8/2001 |
| JP | 2002510222 A | 4/2002 |
| JP | 2002514478 A | 5/2002 |
| JP | 2004173790 A | 6/2004 |
| JP | 2005245215 A | 9/2005 |
| JP | 2010509901 A | 3/2010 |
| JP | 4995090 B2 | 8/2012 |
| JP | 5153892 B2 | 2/2013 |
| NZ | 526115 A | 10/2006 |
| NZ | 539770 A | 10/2007 |
| NZ | 539771 A | 10/2007 |
| WO | 9116864 A1 | 11/1991 |
| WO | 9308871 A1 | 5/1993 |
| WO | 9510226 A1 | 4/1995 |
| WO | 9620754 A1 | 7/1996 |
| WO | 9639932 A1 | 12/1996 |
| WO | 9725098 A1 | 7/1997 |
| WO | 9745157 A1 | 12/1997 |
| WO | 9826840 A1 | 6/1998 |
| WO | 9829030 A1 | 7/1998 |
| WO | 9857592 A1 | 12/1998 |
| WO | 9903533 A1 | 1/1999 |
| WO | 9906102 A1 | 2/1999 |
| WO | 9958191 A1 | 11/1999 |
| WO | 9964104 A1 | 12/1999 |
| WO | 0030534 A1 | 6/2000 |
| WO | 0100114 A1 | 1/2001 |
| WO | 0187137 A2 | 11/2001 |
| WO | 03041793 A2 | 5/2003 |
| WO | 03053491 A2 | 7/2003 |
| WO | 3076010 A1 | 9/2003 |

(56) References Cited

FOREIGN PATENT DOCUMENTS

| WO | 03082403 A2 | 10/2003 |
|---|---|---|
| WO | 03096918 A1 | 11/2003 |
| WO | 03099102 A2 | 12/2003 |
| WO | 2004002572 A1 | 1/2004 |
| WO | 2004012811 A1 | 2/2004 |
| WO | 2004032788 A2 | 4/2004 |
| WO | 2004078025 A2 | 9/2004 |
| WO | 2005058143 A2 | 6/2005 |
| WO | 2005096954 A2 | 10/2005 |
| WO | 2005101660 A1 | 10/2005 |
| WO | 2005107852 A1 | 11/2005 |
| WO | 2005107863 A2 | 11/2005 |
| WO | 2005117737 A2 | 12/2005 |
| WO | 2006045073 A1 | 4/2006 |
| WO | 2006045074 A2 | 4/2006 |
| WO | 2006045075 A1 | 4/2006 |
| WO | 2006096685 A1 | 9/2006 |
| WO | 2007067231 A1 | 6/2007 |
| WO | 2007067253 A1 | 6/2007 |
| WO | 2007078770 A2 | 7/2007 |
| WO | 2007112004 A2 | 10/2007 |
| WO | 2007115044 A2 | 10/2007 |
| WO | 2008011626 A1 | 1/2008 |
| WO | 2007115044 A3 | 2/2008 |
| WO | 2008034005 A2 | 3/2008 |
| WO | 2008034005 A3 | 7/2008 |
| WO | 2008111998 A1 | 9/2008 |
| WO | 2009099550 A1 | 8/2009 |
| WO | 2009099597 A1 | 8/2009 |
| WO | 2012082755 A1 | 6/2012 |

OTHER PUBLICATIONS

"International Application Serial No. PCT/US2007/078405, Written Opinion dated May 20, 2008", p. 237, 7 pgs.
"Japanese Application Serial No. 2008-544324, Response filed Jan. 27, 2012", (w/ English Translation of Amended Claims), 10 pgs.
"Japanese Application Serial No. 2008-544324, Office Action dated May 22, 2012", (w/ English Translation), 5 pgs.
"Japanese Application Serial No. 2008-544324, Office Action dated Nov. 22, 20II", (w/ English Translation), 5 pgs.
"Japanese Application Serial No. 2008-544332, Office Action dated Nov. 29, 20II", (w/ English Translation), 5 pgs.
"U.S. Appl. No. 10/971,550, Notice of Allowance dated Jul. 14, 2008", 4 pgs.
"U.S. Appl. No. 11/549,352, Final Office Action dated Aug. 26, 2008", 13 pgs.
"U.S. Appl. No. 11/549,352, Examiner Interview Summary dated Jun. 25, 2008", 2 pgs.
"U.S. Appl. No. 11/316,120, Response filed May 14, 2008 to Non Final Office Action dated Apr. 11, 2008", 12 pgs.
"U.S. Appl. No. 11/075,375, Non-Final Office Action dated Aug. 11, 2008", 15 pgs.
"U.S. Appl. No. 11/549,352, Non-Final Office Action dated Feb. 5, 2008", 11 pgs.
"U.S. Appl. No. 11/549,352, Pre-Appeal Brief for Review filed Dec. 20, 2008", 5 pgs.
"European Application Serial No. 06790023.3, Office Action dated Mar. 4, 2009", 6 pgs.
"European Application Serial No. 06825988.6, Office Action dated Mar. 4, 2009.", 7 pgs.
"European Application Serial No. 07759589.0, Response filed Jun. 5, 2009 to Office Action dated Jan. 29, 2009", 6 pgs.
"International Application Serial No. PCT/US2009/000693, International Search Report dated May 8, 2009", 5 pgs.
"International Application Serial No. PCT/US2009/000693, Written Opinion dated May 8, 2009", 8 pgs.
"Japanese Application Serial No. 2009-503252, Office Action dated Mar. 21, 2012", (w/ English Translation), 9 pgs.
"Japanese Application Serial No. 2009-503252, Response filed Jun. 20, 2012 to Office Action dated Mar. 21, 2012", (w/ English Claims), 9 pgs.
"Japanese Application Serial No. 2009-503252, Response filed Oct. 26, 2012 to OfficeAction dated Oct. 10, 2012", With English Claims, 6 pgs.
"U.S. Appl. No. 11/745,105, Response filed Jun. 22, 2009 to Restriction Requirement dated May 21, 2009", 6 pgs.
"U.S. Appl. No. 11/075,375, Response filed Jan. 12, 2009 to Non-Final Office Action dated Aug. 11, 2008", 18 pgs.
"U.S. Appl. No. 11/075,376, Final Office Action dated Apr. 8, 2009", 17 pgs.
"U.S. Appl. No. 10/971,550, PTO Response to 312 Amendment dated Apr. 6, 2009", 2 pgs.
"U.S. Appl. No. 11/075,375, Final OfficeAction dated Apr. 16, 2009", 10 pgs.
"U.S. Appl. No. 11/075,375, Notice of Allowance dated Sep. 4, 2009", 6 pgs.
"U.S. Appl. No. 11/511,152, Final Office Action dated Aug. 10, 2009", 13 pgs.
"U.S. Appl. No. 11/745,070, Final OfficeAction dated Dec. 11, 2009", 18 pgs.
"U.S. Appl. No. 11/745,105, Restriction Requirement dated May 21, 2009", 6 pgs.
"U.S. Appl. No. 11/316,120, Final Office Action dated Nov. 12, 2009", 8 pgs.
"U.S. Appl. No. 11/490,916, Final Office Action dated Dec. 17, 2009", 11 pgs.
"U.S. Appl. No. 11/549,352, Examiner's Answer dated Nov. 27, 2009 to Appeal Brief filed Sep. 9, 2009", 12 pgs.
"U.S. Appl. No. 11/549,352, Final OfficeAction dated Mar. 9, 2009", 10 pgs.
"U.S. Appl. No. 11/683,577, Final Office Action dated Nov. 9, 2009", 14 pgs.
"U.S. Appl. No. 11/683,584, Response filed Jul. 1, 2009 to Non Final Office Action dated Apr. 1, 2009", 7 pgs.
"U.S. Appl. No. 11/075,376, Response filed Jul. 8, 2009 to Final Office Action dated Apr. 8, 2009", 11 pgs.
"U.S. Appl. No. 11/490,916, Response filed Sep. 3, 2009 to Non Final Office Action dated May 5, 2009", 13 pgs.
"U.S. Appl. No. 11/490,916, Examiner Interview Summary dated Aug. 19, 2009", 2 pgs.
"U.S. Appl. No. 11/549,352, Notice of Panel Decision from Pre Appeal Brief Review dated Feb. 2, 2009", 2 pgs.
"U.S. Appl. No. 11/683,577, Examiner Interview Summary dated Jul. 7, 2009", 4 pgs.
"U.S. Appl. No. 11/683,584, Examiner Interview Summary dated Jul. 7, 2009", 4 pgs.
"U.S. Appl. No. 11/394,601, Response filed Dec. 2, 2009 to Non Final Office Action dated Sep. 2, 2009", 11 pgs.
"U.S. Appl. No. 11/490,576, Response filed Jun. 17, 2009 to Non Final Office Action dated Feb. 17, 2009", 13 pgs.
"U.S. Appl. No. 11/683,584, Non-Final Office Action dated Apr. 1, 2009", 9 pgs.
"U.S. Appl. No. 11/745,070, Response filed Jul. 27, 2009 to Non Final Office Action dated Apr. 27, 2009", 11 pgs.
"U.S. Appl. No. 11/075,376, Notice of Allowance dated Aug. 24, 2009", 6 pgs.
"U.S. Appl. No. 11/316,120, Response filed Jul. 17, 2009 to Non Final Office Action dated Apr. 17, 2009", 13 pgs.
"U.S. Appl. No. 11/490,576, Non-Final OfficeAction dated Oct. 5, 2009", 8 pgs.
"U.S. Appl. No. 11/511,152, Response filed Mar. 23, 2009 to Non Final Office Action dated Dec. 23, 2008", 11 pgs.
"U.S. Appl. No. 11/745,105, Non Final Office Action dated May 11, 2011", 13 pgs.
"U.S. Appl. No. 11/316,120, Decision on Pre-Appeal Brief Request dated Apr. 19, 2011", 2 pgs.
"U.S. Appl. No. 11/490,576, Decision on Pre-Appeal Brief Request dated Aug. 30, 2011", 2 pgs.
"U.S. Appl. No. 11/490,576, Non Final Office Action dated Nov. 9, 2011", 8 pgs.
"U.S. Appl. No. 12/361,884, Non Final Office Action dated Oct. 12, 2011", 15 pgs.
"U.S. Appl. No. 12/361,884, Preliminary Amendment filed Jun. 30, 2011", 12 pgs.

(56) References Cited

OTHER PUBLICATIONS

"U.S. Appl. No. 12/361,884, Supplemental Preliminary Amendment filed Jul. 27, 2011", 12 pgs.
"U.S. Appl. No. 12/365,428, Non Final Office Action dated Aug. 31, 2011", 9 pgs.
"U.S. Appl. No. 11/490,576, Notice of Allowance dated Jun. 4, 2012", 8 pgs.
"U.S. Appl. No. 11/1490,576, Response filed Apr. 9, 2012 to Non Final Office Action dated Nov. 9, 2011", 11 pgs.
"U.S. Appl. No. 12/910,106, Notice of Allowance dated Jan. 26, 2012", 6 pgs.
"U.S. Appl. No. 12/361,884, Examiner Interview Summary dated Oct. 1, 2012", 3 pgs.
"U.S. Appl. No. 12/365,428, Notice of Allowance dated Feb. 22, 2012", 7 pgs.
"U.S. Appl. No. 11/745,105, Non Final Office Action dated Feb. 7, 2012", 12 pgs.
"U.S. Appl. No. 12/361,884, Response filed Apr. 12, 2012 to Non Final Office Action dated Oct. 12, 2011", 21 pgs.
"U.S. Appl. No. 12/365,428, Response filed Jan. 30, 2012 to Non Final Office Action dated Aug. 31, 2011", 15 pgs.
"U.S. Appl. No. 13/476,599, Examiner Interview Summary dated Dec. 31, 2012", 3 pgs.
"U.S. Appl. No. 13/476,599, Response filed Dec. 19, 2012 to Non Final Office Action dated Aug. 30, 2012", 11 pgs.
"U.S. Appl. No. 12/361,884, Final Office Action dated Jul. 3, 2012", 17 pgs.
"U.S. Appl. No. 11/683,577, Notice of Allowance dated Mar. 5, 2013", 11 pgs.
"U.S. Appl. No. 11/549,352, Restriction Requirement dated Aug. 12, 2013", 5 pgs.
"U.S. Appl. No. 11/854,844, Notice of Allowance dated Sep. 27, 2013", 9 pgs.
"U.S. Appl. No. 13/476,599, Final Office Action dated Aug. 21, 2013", 8 pgs.
"U.S. Appl. No. 12/361,884, Notice of Allowance dated Sep. 25, 2013", 10 pgs.
"U.S. Appl. No. 11/854,844, Response filed May 13, 2013 to Non Final Office Action dated Jan. 11, 2013", 15 pgs.
"U.S. Appl. No. 11/854,844, Non Final Office Action dated Jan. 11, 2013", 15 pgs.
"U.S. Appl. No. 13/717,027 Preliminary Amendment Filed Jun. 25, 2013", 6 pgs.
"U.S. Appl. No. 13/929,286, Non Final Office Action dated Dec. 11, 2013", 15 pgs.
"U.S. Appl. No. 12/361,884, Notice of Allowance dated Jan. 17, 2014", 7 pgs.
"Japanese Application Serial No. 2007-538088, Office Action dated Jun. 13, 2011", (w/ English Translation), 5 pgs.
"Japanese Application Serial No. 2007-538088, Notice of Final Rejection dated Dec. 6, 2011", rwJ English Translation), 9 pgs.
"Japanese Application Serial No. 2007-538087, Response filed Jul. 13, 2012 to Office Action dated Apr. 17, 2012", (w/ English Translation of Amended Claims), 13 pgs.
"Japanese Application Serial No. 2007-538087, Response filed Jun. 27, 2011 to Office Action dated Apr. 11, 2011", (w/ English Translation of Amended Claims), 12 pgs.
"Japanese Application Serial No. 2007-538087, Response filed Mar. 23, 2012 to Office Action dated Oct. 5, 2011", (w/ English Translation of Claims), 9 pgs.
"Japanese Application Serial No. 2007-538087, Office Action dated Oct. 5, 2011", (w/ English Translation), 14 pgs.
"Japanese Application Serial No. 2007-538087, Office Action dated Apr. 17, 2012", w/ English Translation, 8 pgs.
"Japanese Application Serial No. 2007-538087, Office Action dated Apr. 11, 2011", (w/ English Translation), 5 pgs.
"International Application Serial No. PCT/US2009/000693, International Preliminary Report on Patentability dated Aug. 19, 2010", 9 pgs.
"International Application Serial No. PCT/US2009/000587, Written Opinion dated Apr. 24, 2009", 8 pgs.
"International Application Serial No. PCT/US2009/000587, International Search Report dated Apr. 24, 2009", 7 pgs.
"International Application Serial No. PCT/US2009/000587, International Preliminary Report on Patentability dated Aug. 19, 2010", 10 pgs.
"International Application Serial No. PCT/US2007/078405, International Search Report dated May 20, 2008", P220, 7 pgs.
"International Application Serial No. PCT/US2007/078405, International Preliminary Report on Patentability dated Mar. 26, 2009", 9 pgs.
"Telemetry Research Transcutaneous Energy Transfer (TET) Technology Summary", Telemetry Research Ltd; www.telemetryreseacrh.com, (No date listed), 1 page.
Piella, "Energy Management, wireless and system solutions for highly integrated implantable devices", Doctoral Thesis by Jordi Parramon I Piella for the Universitat Autonoma de Barcelona, 62 pages, certified Dec. 2001.
U.S. Appl. No. 11/075,375 Final Office Action dated Jan. 23, 2008, 10 pgs.
"U.S. Appl. No. 11/075,375 Response filed May 22, 2008 to Final Office Action dated Jan. 23, 2008", 16 pages.
U.S. Appl. No. 11/075,376 Restriction Requirement dated Apr. 10, 2007, 6 pgs.
"U.S. Appl. No. 11/075,376 Response filed May 7, 2007 to Restriction Requirement dated Jan. 7, 2007", 1 pg.
"U.S. Appl. No. 10/971,550 Response filed Mar. 25, 2008 to Non Final Office Action dated Nov. 5, 2007", 17 pgs.
"U.S. Appl. No. 11/075,375 Non-Final Office Action dated Jun. 8, 2007", 11 pgs.
"U.S. Appl. No. 11/075,375, Response filed Oct. 26, 2007 to Non-Final Office Action dated Jun. 8, 2007", 10 pgs.
"U.S. Appl. No. 11/075,376 Non-Final Office Action dated Jun. 26, 2007", 9 pgs.
"U.S. Appl. No. 11/075,376, Response filed Oct. 26, 2007 to Non-Final Office Action dated Jun. 26, 2007", 14 pgs.
"U.S. Appl. No. 10/971,550, Non-Final Office Action dated Mar. 19, 2007", 11 pgs.
"U.S. Appl. No. 10/971,550, Non-Final Office Action dated Nov. 5, 2007", 19 pgs.
"U.S. Appl. No. 10/971,550, Response Filed Sep. 4, 2007 to Non-Final Office Action dated Mar. 19, 2007", 15 pgs.
"U.S. Appl. No. 11/075,376, Non-Final Office Action dated Aug. 20, 2008", OARN, 16 pgs.
"U.S. Appl. No. 11/316,120, Final Office Action dated Aug. 20, 2008", FOAR, 9 pgs.
"U.S. Appl. No. 11/490,576, Non Final Office Action dated Jul. 9, 2008", 16 pgs.
"U.S. Appl. No. 12/361,884, Advisory Action dated Sep. 10, 2012", 3 pgs.
U.S. Appl. No. 12/361,884, Response filed Aug. 28, 2012 to Final Office Action dated Jul. 3, 2012, 18 pgs.
"European Application Serial No. 07759589.0, Office Action dated Jan. 29, 2009", 3 pgs.
"International Application No. PCT/US2006/040291 Search Report dated Apr. 4, 2007", 5 pgs.
"International Application No. PCT/US2006/040291 Written Opinion dated Apr. 4, 2007", 9 pgs.
"International Application Serial No. PCT/US2005/037977, International Preliminary Report on Patentability dated Apr. 24, 2007", 9 pgs.
"International Application Serial No. PCT/US2005/037977, International Search Report dated Mar. 21, 2006", 4 pgs.
"International Application Serial No. PCT/US2005/037977,Written Opinion dated Mar. 21, 2006", 8 pgs.
"International Application Serial No. PCT/US2005/037978, International Preliminary Report on Patentability dated Apr. 24, 2007", 13 pgs.
"International Application Serial No. PCT/US2005/037979, International Preliminary Report on Patentability dated Apr. 24, 2007", 9 pgs.

(56) References Cited

OTHER PUBLICATIONS

"International Application Serial No. PCT/US2006/033414, International Preliminary Reporton Patentability dated Jun. 19, 2008", 11 pgs.
"International Application Serial No. PCT/US2006/033414, International Search Report dated Mar. 1, 2007", 5 pgs.
"International Application Serial No. PCT/US2006/033414, Written Opinion dated Mar. 1, 2007", 9 pgs.
"International Application Serial No. PCT/US2006/040291, International Preliminary Reporton Patentability dated Jun. 19, 2008", 11 pgs.
"International Application Serial No. PCT/US2006/047553, International Preliminary Report on Patentability dated Apr. 3, 2008", 8 pgs.
"International Application Serial No. PCT/US2006/047553, International Search Report dated Jun. 20, 2007", 3 pgs.
International Application Serial No. PCT/US2006/047553, Written Opinion dated Jun. 20, 2008, 7 pgs.
"International Application Serial No. PCT/US2007/065376, International Preliminary Report on Patentability dated Oct. 9, 2008", 10 pgs.
"International Application Serial No. PCT/US2007/065376, International Search Report dated Dec. 14, 2007", 5 pgs.
"International Application Serial No. PCT/US2007/065376, Written Opinion dated Dec. 14, 2007", 11 pgs.
"International Application Serial No. PCT/US2007/074125, International Preliminary Reporton Patentability dated Feb. 5, 2009", 9 pgs.
"International Application Serial No. PCT/US2007/074125, International Search Report dated Dec. 6, 2007", 4 pgs.
"International Application Serial No. PCT/US2007/074125, Writen Opinion dated Dec. 6, 2007", 8 pgs.
"International Application Serial No. PCT/US2007/074135, International Preliminary Reporton Patentability dated Feb. 5, 2009", 9 pgs.
"U.S. Appl. No. 10/971,550, Notice of Allowance dated Dec. 22, 2008", 4 pgs.
"U.S. Appl. No. 11/075,375, Restriction Requirement dated Apr. 10, 2007", 6 pgs.
"U.S. Appl. No. 11/075,375, Response filed Jul. 16, 2009 to Final Office Action dated Apr. 16, 2009", 13 pgs.
"U.S. Appl. No. 11/075,376, Response filed May 7, 2007 to Restriction Requirement dated Apr. 10, 2007", 10 pgs.
"U.S. Appl. No. 11/549,352, Appeal Brief filed Sep. 9, 2009", 36 pgs.
"U.S. Appl. No. 11/683,584, Notice of Allowance dated Aug. 7, 2012", 6 pgs.
"U.S. Appl. No. 11/693,584, Preliminary Amendment filed Mar. 8, 2007", 1 pg.
"U.S. Appl. No. 11/745,105, Notice of Allowance dated Aug. 20, 2012", 5 pgs.
"U.S. Appl. No. 11/745,105, Response filed Aug. 6, 2012 to Non Final Office Action dated Feb. 7, 2012", 11 pgs.
"U.S. Appl. No. 11/549,352, Appeal Decision dated Jul. 17, 2012", 9 pgs.
"U.S. Appl. No. 11/394,601, Response filed May 4, 2009 to Restriction Requirement dated Apr. 2, 2009", 9 pgs.
"U.S. Appl. No. 11/075/376 Final Office Action dated Jan. 7, 2008", 11 pgs.
"U.S. Appl. No. 11/075/376 Response filed Jun. 9, 2008 to Final Office Action dated Jan. 7, 2008", 20 pages.
"Japanese Application Serial No. 2008-544332, Response filed Mar. 19, 2012 to Office Action dated Nov. 29, 2011", (w/ English Translation of Claims), 9 pgs.
"U.S. Appl. No. 11/549,532 Response filed Jul. 7, 2008 to Non Final Office Action dated Feb. 5, 2008," 17 pgs.
"Japanese Application Serial No. 2007-538088, Response filed Mar. 27, 2012 to Final Office Action dated Dec. 6, 2011", (w/ English Translation of Claims), 11 pgs.
"Japanese Application Serial No. 2007-538088, Response filed Aug. 25, 2011 to Office Action dated Jun. 13, 2011", (w/ English Translation of Amended Claims), 9 pgs.
"Japanese Application Serial No. 2007-538089, Office Action dated Mar. 3, 2011", (w/ English Translation).
"Japanese Application Serial No. 2007-538089, Response filed May 25, 2011 to Office Action dated Mar. 3, 2011", (w/ English Translation of Amended Claims), 8 pgs.
"Japanese Application Serial No. 2010-545866, Office Action dated Jun. 5, 2012", (w/ English Translation), 5 pgs.
"Japanese Application Serial No. 2010-545866, Response filed Sep. 5, 2012 to Office Action dated Jun. 5, 2012", (w/ English Translation of Amended Claims), 12 pgs.
Monoharan et al; "Novel Passive Implantable Atrial Defibrillator Using Transcutaneous Radiofrequency Energy Transmission Successfully Cardioverts Atrial Fibrillation" for Circulation,QQ. 1382-1388, Sep. 16, 2003.
"PCT Application No. PCT/US2005/037979, International Search Report dated Mar. 21, 2006", 4 pgs.
"PCT Application No. PCT/US2005/037979, Written Opinion dated Mar. 21, 2006", 8 pgs.
"PCT Application No. PCT/US2007/074135, International Search Report dated Nov. 6, 2007", 4 pgs.
"PCT Application No. PCT/US2007/074135, Written Opinion dated Nov. 6, 2007", 8 pgs.
Busch, M., et al., "On the Heating of Inductively Coupled Resonators (Stents) During MRI Examinations", Maanetic Resonance in Medicine 54, (2005), 775-785.
Si, et al., "A Frequency Control Method for Regulating Wireless Power to Implantable Devices", IEEE Transactions on Biomedical Circuits and Systems, 2(1), (Mar. 2008), 22-29.
Swain, E., "Breakthrough Products Could Put Lesser-Known Firms on the Map", (c) 2004 Medical Device & Diagnostic Industrv, [online]. Retrieved from the Internet: <URL: http://www.devicelink.com/mddi/archive/04/04/006.html>, (Apr. 2004), 6 pgs.
Wagner, "Electrodes, Leads, and Biocompatibility," Design of Cardiac Pacemakers, 1993, Chapter 6, pp. 133-160 and TOC.
U.S. Appl. No. 12/361,884, Response filed Oct. 3, 2012 to Final Office Action dated Jul. 3, 2012, 18 pgs.
"U.S. Appl. No. 13/476,599, Non Final Office Action dated Aug. 30, 2012", 6 pgs.
European Application Serial No. 05815206.7, Communication dated Dec. 18, 2009, 4 pgs.
"European Application Serial No. 05815206.7, Office Action dated May 16, 2012", 5 pgs.
"European Application Serial No. 05815206.7, Office Action dated Sep. 12, 2012", 27 pgs.
"European Application Serial No. 05815206.7, Response filed Apr. 19, 2010 to Communication dated Dec. 18, 2009", 27 pgs.
"European Application Serial No. 05815215.8, Communication dated Dec. 18, 2009", 2 pgs.
"European Application Serial No. 05815215.8, Response filed Mar. 19, 2010 to Communication dated Dec. 18, 2009", 12 pgs.
"European Application Serial No. 05817448.3, Communication dated Dec. 18, 2009", 2 pgs.
"European Application Serial No. 05817448.3, Office Action dated May 16, 2012", 5 pgs.
"European Application Serial No. 05817448.3, Response filed Mar. 19, 2010 to Communication dated Dec. 18, 2009", 9 pgs.
"European Application Serial No. 05817448.3, Response filed Sep. 14, 2012 to Office Action dated May 16, 2012", 14 pgs.
"European Application Serial No. 06790023.3 Response filed Sep. 14, 2009 to Office Action dated Mar. 4, 2009", 11 pgs.
"European Application Serial No. 06825988.6, Response filed Sep. 14, 2009 to Office Action dated Mar. 4, 2009", 12 pgs.
"European Application Serial No. 06847612.6, Office Action dated May 26, 2009", 3 pgs.
"European Application Serial No. 06847612.6, Office Action dated Dec. 7, 2010", 4 pgs.
"European Application Serial No. 06847612.6, Response filed Apr. 12, 2011 to Office Action dated Dec. 7, 2010", 5 pgs.
"European Application Serial No. 06847612.6, Response filed Oct. 26, 2009 to Office Action dated May 26, 2009", 12 pages.

(56) References Cited

OTHER PUBLICATIONS

"European Application Serial No. 06847612.6, Summons to Attend Oral Proceedings dated Jun. 20, 2012", 3 pgs.

"European Application Serial No. 07759589.0, Summons to Attend Oral Proceedings dated May 17, 2011", 3 pages.

European Application Serial No. 07759589.0, Written Submission filed Dec. 5, 2011 to Summon to Attend Oral Procedings dated May 17, 2011, 16 pgs.

"European Application Serial No. 09709347.0, Office Action dated Oct. 4, 2010", 1 pg.

"European Application Serial No. 09709347.0 Response filed Oct. 28, 2010 to Office Action dated Oct. 4, 2010", 7 pgs.

"International Application Serial No. PCT/US2005/037978, Written Opinion dated Jun. 13, 2006", 12 pgs.

"U.S. Appl. No. 11/075,376, Response filed Jan. 21, 2009 to Non-Final Office Action dated Aug. 20, 2008", 22 pages.

"U.S. Appl. No. 11/316,120, Response filed Dec. 22, 2008 to Final Office Action dated Aug. 20, 2008", 13 pages.

"U.S. Appl. No. 11/490,576, Response filed Nov. 10, 2008 to Non-Final Office Action dated Jul. 9, 2008", 20 pages.

U.S. Appl. No. 11/490,916, Restriction Requirement dated Dec. 11, 2008, 8 pgs.

U.S. Appl. No. 11/511,152, Non-Final Office Action dated Dec. 23, 2008, 14 pgs.

"U.S. Appl. No. 10/971,550 Restriction Requirement dated Jan. 22, 2007", 22 pgs.

"U.S. Appl. No. 10/971,550 Response filed Feb. 22, 2007 to Restriction Requirement dated Jan. 22, 2007", 1 pg.

"U.S. Appl. No. 11/075,375 Response Filed May 7, 2007 to Restriction Requirement dated Apr. 10, 2007", 8 pgs.

"U.S. Appl. No. 11/683,577, Response filed Aug. 5, 2009 to Non Final Office Action dated Mar. 5, 2009", 10 pgs.

"U.S. Appl. No. 10/971,550, 312 Amendment filed Mar. 20, 2009", 6 pgs.

"U.S. Appl. No. 11/394,601, Restriction Requirement dated Apr. 2, 2009", 10 pgs.

"U.S. Appl. No. 11/683,577, Non-Final Office Action dated Mar. 5, 2009", 13 pgs.

"U.S. Appl. No. 11/745,070, Non Final Office Action dated Apr. 27, 2009", 11 pgs.

"U.S. Appl. No. 11/745,105, Non-Final Office Action dated Sep. 18, 2009", 9 pgs.

"U.S. Appl. No. 11/316,120, Non-Final Office Action dated Apr. 17, 2009", 8 pgs.

"U.S. Appl. No. 11/394,601, Non-Final Office Action dated Sep. 2, 2009", 6 pgs.

"U.S. Appl. No. 11/490,576, Non-Final Office Action dated Feb. 17, 2009", 8 pgs.

"U.S. Appl. No. 11/490,916, Non Final Office Action dated May 5, 2009", 10 pgs.

"U.S. Appl. No. 11/511,152, Non-Final Office Action dated Dec. 30, 2009", 13 pgs.

"U.S. Appl. No. 11/511,152, Response filed Nov. 12, 2009 to Final Office Action dated Aug. 10, 2009", 13 pgs.

"European Application Serial No. 07759589.0, Office Action dated Feb. 18, 2010", 3 pgs.

"European Application Serial No. 07759589.0, Response filed Jun. 24, 2010 to Office Action dated Feb. 18, 2010", 3 pgs.

"U.S. Appl. No. 11/511,152, Response filed Jun. 30, 2010 to Non-Final Office Action dated Dec. 30, 2009", 12 pgs.

"U.S. Appl. No. 11/316,120, Final Office Action dated Oct. 28, 2010", 8 pgs.

"U.S. Appl. No. 11/490,916, Notice of Allowance dated Jul. 9, 2010", 4 pgs.

"U.S. Appl. No. 11/511,152, Notice of Allowance dated Jul. 28, 2010", 6 pgs.

"U.S. Appl. No. 11/745,105, Final Office Action dated Mar. 30, 2010", 9 pgs.

"U.S. Appl. No. 11/394,601, Final Office Action dated Mar. 22, 2010", 7 pgs.

"U.S. Appl. No. 11/394,601, Notice of Allowance dated Dec. 28, 2010", 8 pgs.

"U.S. Appl. No. 11/490,576, Response filed Oct. 4, 2010 to Non Final Office Action dated Jul. 12, 2010", 15 pgs.

"U.S. Appl. No. 11/683,584, Final Office Action dated Jan. 29, 2010", 9 pgs.

"U.S. Appl. No. 11/490,916, Examiner Interview Summary dated Apr. 12, 2010", 3 pgs.

"U.S. Appl. No. 11/490,916, Supplemental Notice of Allowability dated Oct. 14, 2010", 2 pgs.

"U.S. Appl. No. 11/490,576, Response filed Mar. 5, 2010 to Non Final Office Action dated Oct. 5, 2009", 13 pgs.

"U.S. Appl. No. 11/683,577, Response filed May 7, 2010 to Final Office Action dated Nov. 9, 2009", 14 pgs.

"U.S. Appl. No. 11/745,105, Response filed Jan. 19, 2010 to Non Final Office Action dated Sep. 18, 2009", 12 pgs.

"U.S. Appl. No. 11/745,105, Response filed Jul. 29, 2010 to Final Office Action dated Mar. 30, 2010", 12 pgs.

"U.S. Appl. No. 11/316,120, Response filed Apr. 12, 2010 to Final Office Action dated Nov. 12, 2009", 12 pgs.

"U.S. Appl. No. 11/316,120, Response filed Aug. 27, 2010 to Non Final Office Action dated May 27, 2010", 13 pgs.

"U.S. Appl. No. 11/490,916, Response filed Apr. 15, 2010 to Final Office Action dated Dec. 17, 2009", 12 pgs.

"U.S. Appl. No. 11/683,584, Response filed Jul. 21, 2010 to Final Office Action dated Jan. 29, 2010", 12 pgs.

"U.S. Appl. No. 11/316,120, Non-Final Office Action dated May 27, 2010", 7 pgs.

"U.S. Appl. No. 11/394,601, Decision on Pre-Appeal Brief Request dated Oct. 6, 2010", 2 pgs.

"U.S. Appl. No. 11/394,601, Pre-Appeal Brief Request filed Jul. 21, 2010", 5 pgs.

"U.S. Appl. No. 11/490,576, Non-Final Office Action dated Jul. 12, 2010", 8 pgs.

"U.S. Appl. No. 11/549,352, Reply Brief filed Jan. 27, 2010", 8 pgs.

"U.S. Appl. No. 11/745,105, Response filed Sep. 12, 2011 to Non-Final Office Action dated May 11, 2011", 13 pgs.

"U.S. Appl. No. 12/910,106, Response filed Aug. 2, 2011 to Non-Final Office Action dated Apr. 4, 2011", 14 pgs.

"U.S. Appl. No. 11/745,105, Notice of Allowance dated Oct. 31, 2011", 5 pgs.

"U.S. Appl. No. 11/316,120, Supplemental Notice of Allowance dated Sep. 1, 2011", 4 pgs.

"U.S. Appl. No. 11/316,120, Notice of Allowance dated Jul. 20, 2011", 7 pgs.

"U.S. Appl. No. 11/490,576, Final Office Action dated Jan. 19, 2011", 12 pgs.

"U.S. Appl. No. 12/910,106, Notice of Allowance dated Oct. 27, 2011", 5 pgs.

"U.S. Appl. No. 11/316,120, Response filed Mar. 25, 2011 to Final Office Action dated Oct. 28, 2010", 8 pgs.

"U.S. Appl. No. 11/490,576, Pre-Appeal Brief Request filed May 12, 2011", 5 pgs.

"U.S. Appl. No. 11/316,120, Pre-Appeal Brief Request filed Mar. 25, 2011", 5 pgs.

"U.S. Appl. No. 12/910,106, Non Final Office Action dated Apr. 4, 2011", 9 pgs.

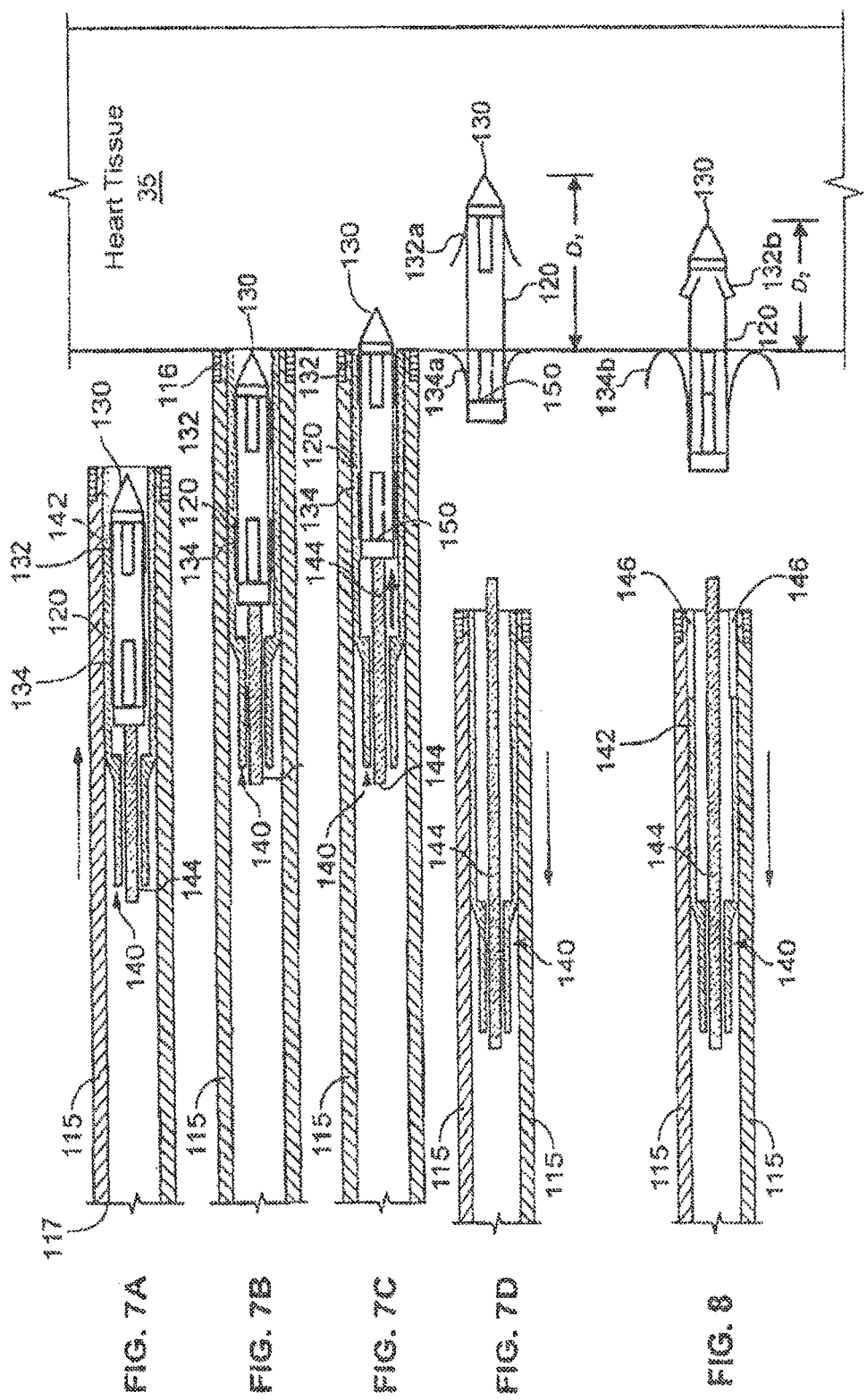

CARDIAC STIMULATION SYSTEM

CROSS REFERENCE TO RELATED APPLICATION

This application is a continuation of U.S. application Ser. No. 16/008,562, filed Jun. 14, 2018, which is a continuation of U.S. application Ser. No. 14/044,094, filed Oct. 2, 2013, now U.S. Pat. No. 10,022,538 which is a continuation of U.S. application Ser. No. 11/549,352, filed Oct. 13, 2006, now abandoned, which claims priority to U.S. Provisional Application Ser. No. 60/748,964 filed on Dec. 9, 2005, the contents of each of which are incorporated herein by reference.

TECHNICAL FIELD

This document relates to systems that electrically stimulate cardiac or other tissue.

BACKGROUND

Pacing instruments can be used to treat patients suffering from a heart condition, such as a reduced ability to deliver sufficient amounts of blood from the heart. For example, some heart conditions may cause or be caused by conduction defects in the heart. These conduction defects may lead to irregular or ineffective heart contractions. Some pacing instruments (e.g., a pacemaker) may be implanted in a patient's body so that pacing electrodes in contact with the heart tissue provide electrical stimulation to regulate electrical conduction in the heart tissue. Such regulated electrical stimulation may cause the heart to contract and hence pump blood.

Conventionally, pacemakers include a pulse generator that is implanted, typically in a patient's pectoral region just under the skin. One or more wired leads extend from the pulse generator so as to contact various portions of the heart. An electrode at a distal end of a lead may provide the electrical contact to the heart tissue for delivery of the electrical pulses generated by the pulse generator and delivered to the electrode through the lead.

The use of wired leads may limit the number of sites of heart tissue at which electrical energy may be delivered. For example, most commercially available pacing leads are not indicated for use in the left side of the heart. One reason is that the high pumping pressure on the left side of the heart may cause a thrombus or clot that forms on a bulky wired lead to eject into distal arteries, thereby causing stroke or other embolic injury. Thus, in order to pace the left side of the heart with a wired lead, most wired leads are directed through the cardiac venous system to a site (external to the left heart chambers) in a cardiac vein over the left side of the heart. While a single lead may occlude a cardiac vein over the left heart locally, this is overcome by the fact that other cardiac veins may compensate for the occlusion and deliver more blood to the heart. Nevertheless, multiple wired leads positioned in cardiac veins can cause significant occlusion, thereby limiting the number of heart tissue sites at which electrical energy may be delivered to the left side of the heart.

Some pacing systems may use wireless electrodes that are attached to the epicardial surface of the heart (external to the heart chambers) to stimulate heart tissue. In these systems, the wireless electrodes are screwed into the outside surface of the heart wall, which can reduce the effectiveness of the electrical stimulation in some circumstances.

SUMMARY

Some embodiments of pacing systems employ wireless electrode assemblies to provide pacing therapy. The wireless electrode assemblies may receive energy via an inductive coupling so as to provide electrical stimulation to the surrounding heart tissue. In certain embodiments, a wireless electrode assembly may be directed through a guide catheter in a heart chamber to deliver at least a portion of the wireless electrode assembly through the endocardium. For example, the electrode assembly may include first and second fixation devices to secure the electrode assembly to the heart chamber wall. In such circumstances, the first fixation device may oppose rearward migration of the electrode assembly out of the heart chamber wall, and the second fixation device may oppose forward migration into the heart chamber wall. Accordingly, the wireless electrode assembly can be readily secured to the heart chamber wall and incorporated into the surrounding heart tissue over a period of time.

In some embodiments, a wireless electrode assembly may include a body portion that at least partially contains a circuit to electrically stimulate an electrode. The wireless electrode assembly may also include first and second biased tines to shift from a loaded condition to an outwardly extended condition to secure the body portion to a heart chamber wall. The first and second biased tines may be generally opposed to one another.

Particular embodiments may include an electrode delivery system for delivering a wireless electrode assembly into a heart chamber. The system may include a wireless electrode assembly including a body portion and first and second biased tines to shift from a loaded condition to an outwardly extended condition to secure the body portion to a heart chamber wall. The first and second biased tines may oppose one another. The system may also include a delivery catheter to direct the wireless electrode assembly through a heart chamber and toward a heart chamber wall. The delivery catheter may include an opening in a distal end such that, when the wireless electrode assembly is separated from the opening in the distal end of the catheter, the first and second biased tines shift from the loaded condition to the outwardly extended condition.

Some embodiments may include a method of inserting a wireless electrode assembly into a heart chamber wall. The method may include inserting a first biased tine of a wireless electrode assembly through a portion of endocardium and into a heart chamber wall. The first biased tine may shift from a loaded condition to an outwardly extended condition to secure the body portion to a heart chamber wall. The method may also include causing a second biased tine of the wireless electrode assembly to shift from the loaded condition to the outwardly extended condition to secure the body portion to a heart chamber wall. The first and second biased tines may be generally opposed to one another when in their respective outwardly extended conditions.

These and other embodiments described herein may provide one or more of the following advantages. First, the wireless electrode assemblies may eliminate or otherwise limit the need for wired pacing leads, thereby reducing the risk of stroke or other embolic injury from a thrombus or clot and reducing the risk of occluding cardiac veins (external to the heart chambers). Second, the wireless electrode assemblies may be secured to the inner wall of one more heart chambers, which may provide more efficient transfer of electrical stimulation. Third, the wireless electrode assemblies may be secured to a heart chamber wall in a manner that opposes both forward migration and rearward migration of the electrode assembly. In such circumstances, the secure attachment of the wireless electrode assembly with the heart wall may increase the likelihood of incorporating the electrode assembly into surrounding tissue, thereby further reducing the likelihood of forming a thrombus or clot in the heart chamber.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 7A-D are partial cross-sectional views of the delivery of the wireless electrode assembly of FIG. 5.

FIG. 8 is a partial cross-sectional view of the delivery of the wireless electrode assembly of FIG. 6.

Like reference symbols in the various drawings indicate like elements.

DETAILED DESCRIPTION OF ILLUSTRATIVE EMBODIMENTS

Figure 1:
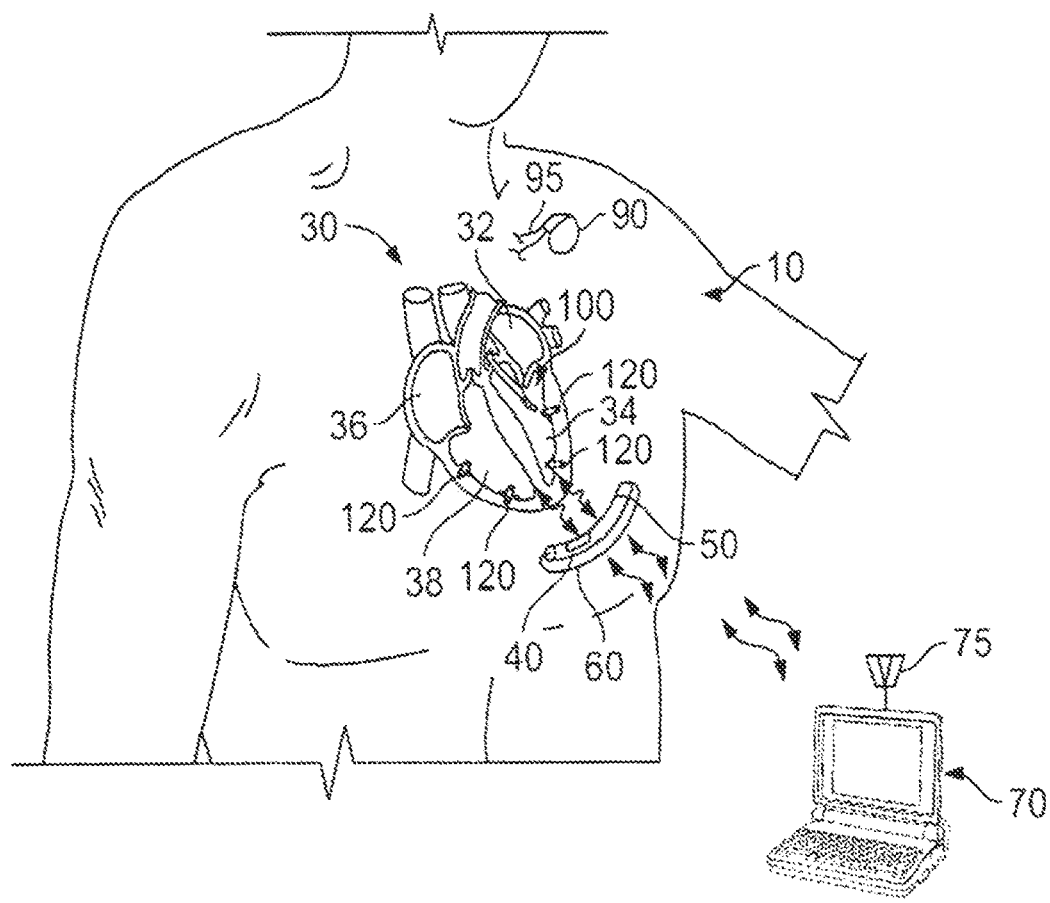
FIG. 1 is a perspective view of a stimulation system and at least a portion of an electrode delivery system, in accordance with some embodiments of the invention.

Referring to FIG. 1, an electrical stimulation system 10 may include one or more wireless electrode assemblies 120. The wireless electrode assemblies 120 are implanted within chambers of the heart 30. In this example, there are two implanted in the left ventricle 34 and two implanted in the right ventricle 38, but the wireless electrode assemblies may be implanted in the left atrium 32, the right atrium 36, or both. As described below in connection with FIGS. 4-8, the wireless electrode assemblies 120 may be delivered to one or more chambers of the heart 30 using an electrode delivery system 100. The electrode delivery system may include a guide catheter 110 that is directed through one or more veins or arteries to the targeted chamber of the heart 30 (e.g., the left ventricle 34 is the targeted chamber in the embodiment shown in FIG. 1). After the guide catheter 110 is deployed into the targeted heart chamber the wireless electrode assemblies 120 may be consecutively delivered through the guide catheter 110 using at least one delivery catheter 115, which may include a steering mechanism (e.g., steering wires, a shape memory device, or the like) to delivery the wireless electrode assembly 120 to the targeted site on the heart chamber wall.

The distal end of each wireless electrode assembly 120 may include one or more fixation devices, such as tines. As described in more detail below in connection with FIGS. 5 and 6, the tines 132 and 134 can secure the wireless electrode assembly 120 to the heart chamber wall. In some embodiments, each of the wireless electrode assemblies 120 may include a circuit comprising an internal coil and an electrical charge storage device (not shown in FIG. 1). As described in more detail below in connection with FIG. 3, the internal coil can be inductively coupled with an external power source coil so as to charge the electrical charge storage device (e.g., a battery, capacitor or the like) contained within the wireless electrode assembly 120. Also, in some embodiments, each of the wireless electrode assemblies 120 has a triggering mechanism in the circuit to deliver stored electrical charge to adjacent heart tissue (some examples are described in more detail below in connection with FIG. 3). In alternative embodiments, one or more of the wireless electrode assemblies 120 may have no energy storage device. In such circumstances, each wireless electrode assembly may be comprised, for example, of a ferrite core having caps at each end with ring electrodes encircling the caps. A number of turns of fine insulated wire may be wrapped around the central portion of the core so as to receive energy from a magnetic field produced by a shaped driving signal and designed to activate the electrodes.

Referring still to FIG. 1, the system 10 may also include a pacing controller 40 and a transmitter 50 that drives an antenna 60 for communication with the wireless electrode assemblies 120. The pacing controller 40 includes circuitry to sense and analyze the heart's electrical activity, and to determine if and when a pacing electrical pulse needs to be delivered and by which of the wireless electrode assemblies 120. The sensing capability may be made possible by having sense electrodes included within the physical assembly of the pacing controller 40. Alternatively, a conventional single or dual lead pacemaker may sense the local cardiac electrocardiogram (ECG) and transmit this information to antenna 60 for use by controller 40 in determination of the timing of wireless electrode assembly firing. In either case, the wireless electrode assembly 120 need not be provided with sensing capability, and also the wireless electrode assemblies 120 need not be equipped with the capability of communicating to the pacing controller 40 (for example, to communicate information about sensed electrical events). In alternative embodiments, the wireless electrode assemblies may communicate sensed information to each other and/or to the controller 40.

The transmitter 50—which is in communication with, and is controlled by, the pacing controller 40—may drive an RF signal onto the antenna 60. In one embodiment, the transmitter 50 provides both (1) a charging signal to charge the electrical charge storage devices contained within the wireless electrode assemblies 120 by inductive coupling, and (2) an information signal, such as a pacing trigger signal, that is communicated to a selected one or more of the wireless electrode assemblies 120, commanding that wireless electrode assembly 120 deliver its stored charge to the adjacent heart tissue.

One parameter of the wireless electrode assembly 120 that may affect the system design is the maximum energy required to pace the ventricle 34, 38 or other chamber of the heart 30. This energy requirement can include a typical value needed to pace ventricular myocardium, but also can include a margin to account for degradation of contact between the electrodes and tissue over time. In certain embodiments, each wireless electrode assembly 120 may require the maximum pacing threshold energy. This threshold energy is supplied to the wireless electrode assemblies between heartbeats by an external radio frequency generator (which may also be implanted), or other suitable energy source that may be implanted within the body. Parameter values for some embodiments may be:

Threshold pacing voltage=2.5 Volts
Typical lead impedance=600 Ohms
Typical pulse duration=0.4 mSec
Derived threshold energy=4 micro-Joules Because RF fields at frequencies higher than about 200 kHz may be attenuated by the body's electrical conductivity and because electric fields of any frequency may be attenuated within the body, energy transmission through the body may be accomplished in some embodiments via a magnetic field at about 20-200 kHz (or by a magnetic field pulse that contains major frequency components in this range) and preferably by transmission of magnetic fields in the range of 100-200 kHz when transmission is through relatively conductive blood and heart muscle.

Still referring to FIG. 1, the pacing controller 40 and the transmitter 50 may be housed in a single enclosure that is implantable within a patient. In such a configuration, the single enclosure device may have a single energy source (battery) that may be either rechargeable or non-rechargeable. In another configuration, the pacing controller 40 and the transmitter 50 may be physically separate components. As an example of such a configuration, the pacing controller 50 may be implantable, for example in the conventional pacemaker configuration, whereas the transmitter 50 (along with the antenna 60) may be adapted to be worn externally, such as in a harness that is worn by the patient. In the latter example, the pacing controller 40 would have its own energy source (battery), and that energy would not be rechargeable given the relatively small energy requirements of the pacing controller 40 as compared to the energy requirements of the transmitter 50 to be able to electrically charge the wireless electrode assemblies 120. In this case, the pacing controller 40 would sense the local cardiac ECG signal through a conventional pacing lead, and transmit the sensed information to the external controller. Again, transmission of information, as opposed to pacing energy, has a relatively low power requirement, so a conventional pacemaker enclosure and battery would suffice.

The external programmer 70 is used to communicate with the pacing controller 40, including after the pacing controller 40 has been implanted. The external programmer 70 may be used to program such parameters as the timing of stimulation pulses in relation to certain sensed electrical activity of the heart, the energy level of stimulation pulses, the duration of stimulation pulse (that is, pulse width) etc. The programmer 70 includes an antenna 75 to communicate with the pacing controller 40, using, for example, RF signals. The implantable pacing controller 40 is accordingly equipped to communicate with the external programmer 70, using, for example, RF signals. The antenna 60 may be used to provide such communications, or alternatively, the pacing controller 40 may have an additional antenna (not shown in FIG. 1) for external communications with the programmer 70, and in an embodiment where the transmitter 50 and antenna 60 are housed separately from the controller 40, for communications with the transmitter 50.

Still referring to FIG. 1, at least a portion of the system 10 is shown as having been implanted in a patient, and in addition, the programmer 70 is also shown that is external to the patient. The controller 40 and transmitter 50 may be housed in a device that is shaped generally elongate and slightly curved so that it may be anchored between two ribs of the patient, or possibly around two or more ribs. In one example, the housing for the controller 40 and transmitter 50 is about 2 to 20 cm long and about 1 to 10 centimeters cm in diameter, may be about 5 to 10 cm long and about 3 to 6 cm in diameter. Such a shape of the housing for the controller 40 and transmitter 50, which allows the device to be anchored on the ribs, may provide an enclosure that is larger and heavier than conventional pacemakers, and may provide a larger battery having more stored energy. In addition, the controller 40 may comprise a defibrillator that discharges energy to the heart 30 through electrodes on the body of controller 40 when fibrillation is sensed. Other sizes and configurations may also be employed as is practical.

In some embodiments, the antenna 60 may be a loop antenna comprised of a long wire that is electrically connected across an electronic circuit contained within the controller/transmitter housing, which circuit delivers pulses of RF current to the antenna 60, generating a magnetic field in the space around the antenna 60 to charge the wireless electrode assemblies 120, as well as RF control magnetic field signals to command the wireless electrode assemblies 120 to discharge. In such embodiments, the antenna 60 may comprise a flexible conductive material so that it may be manipulated by a physician during implantation into a configuration that achieves improved inductive coupling between the antenna 60 and the coils within the implanted wireless electrode assemblies 120. In one example, the loop antenna 60 may be about 2 to 22 cm long, and about 1 to 11 cm wide, and may be about 5 to 11 cm long, and about 3 to 7 cm wide. Placement of the antenna 60 over the ribs may provide a relatively large antenna to be constructed that has improved efficiency in coupling RF energy to the pacing wireless electrode assemblies 120.

As shown in FIG. 1, some embodiments of the system 10 may also include a pulse generator device 90 (or pacemaker device) and associated wired leads 95 which extend from the pulse generator device 90 and into one or more chambers of the heart 30 (e.g., into the right atrium 36). For example, the system 10 may include wired leads 95 from the pulse generator device 90 that extend into the right atrium 36 and the right ventricle 38 while wireless electrode assemblies are disposed in the left atrium 32 and the left ventricle 34. The pulse generator device 90 may be used to sense the internal ECG, and may also communicate with the controller 40 and/or transmitter 50 as previously described.

As previously described, in some embodiments, each of the wireless electrode assemblies 120 includes a rechargeable battery or other charge storage device. This battery may provide power for delivering pacing energy to the tissue, and for operating communications, logic, and memory circuitry contained within the assembly. In some alternative embodiments, a transmitter and an antenna may be external to the patient (as opposed to the implantable transmitter 50 and antenna 60 depicted in FIG. 1), and may serve to recharge the batteries within the electrode assemblies. The recharge transmitter and antenna may be incorporated into furniture, incorporated into the patient's bed, or worn by the patient (e.g., in a vest-type garment). Daily recharging for predetermined to periods (e.g., about 30 minutes) may be required in some cases. In these circumstances, the wireless electrode assemblies 120 may be autonomous pacemaker-like devices, which can sense the local electrogram and only pace when the local tissue is not refractory. Such electrodes may communicate with the programming unit 70 to receive pacing instructions and transmit data stored in local memory. In these embodiments, each wireless electrode assembly 120 may also communicate with other implanted wireless electrode assemblies 120. For example, one electrode assembly 120 in the right atrium may be designated as the "master,"

and all other implanted electrodes are "'slaves," that pace with pre-programmed delays relative to the "'master." As such, a master electrode in the right atrium may only sense the heart's sinus rhythm, and trigger pacing of the slaves with programmed delays.

Figure 2:
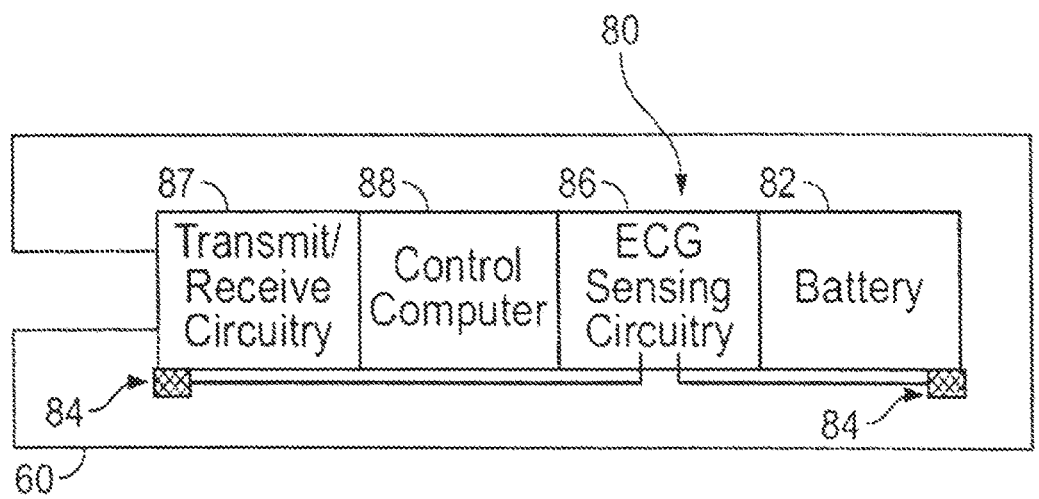
FIG. 2 is a diagram of at least a portion of a device of the stimulation system of FIG. 1.

Referring to FIG. 2, an embodiment of a device 80 including the controller 40, transmitter 50, associated antenna 60 is shown in block diagram form. Included within the device 80 is: a battery 82, which may be recharged by receiving RF energy from a source outside the body via antenna 60; ECG sensing electrodes 84 and associated sensing circuitry 86; circuitry 87 for transmitting firing commands to the implanted wireless electrode assemblies, transmitting status information to the external programmer, receiving control instructions from the external programmer and receiving power to recharge the battery; and a controller or computer 88 that is programmed to control the overall functioning of the pacing control implant. In alternative embodiments, antenna 60 may receive signals from the individual wireless electrode assemblies 120 containing information regarding the local ECG at the site of each wireless electrode assembly, and/or the antenna 60 may receive signals from a more conventional implanted pacemaker regarding the ECG signal at the sites of one or more conventional leads implanted on the right side of the heart.

Figure 3:
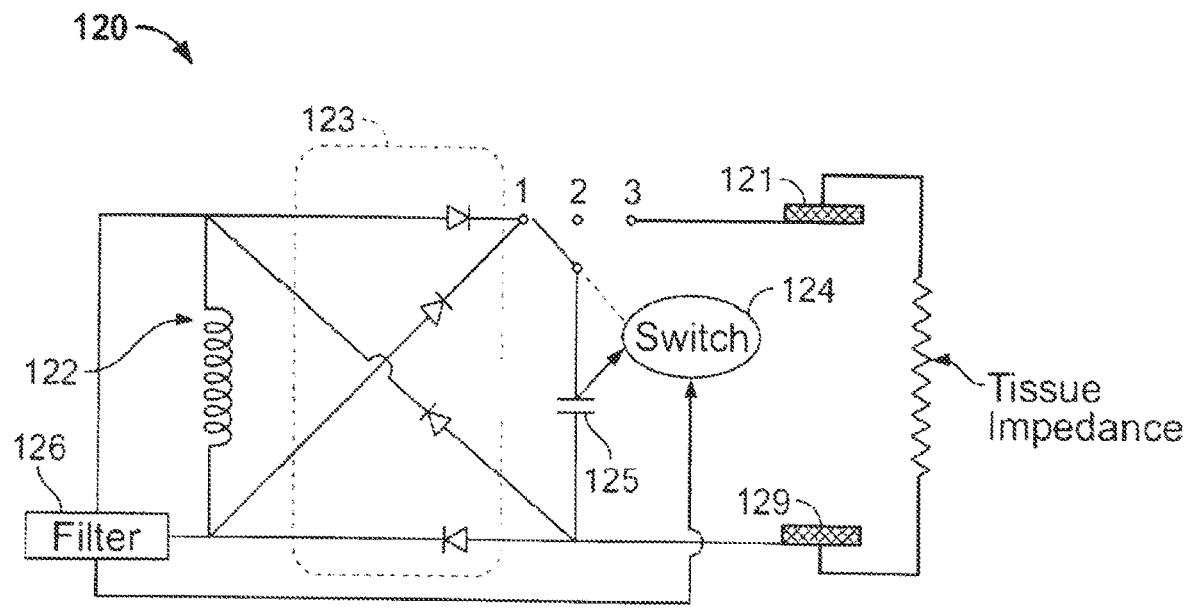
FIG. 3 is a diagram of at least a portion of a wireless electrode assembly of the stimulation system of FIG. 1.

Referring to FIG. 3, some embodiments of a wireless electrode assembly 120 may include a receiver coil 122 that is capable of being inductively coupled to a magnetic field source generating a time-varying magnetic field at the location of coil 122, such as would be generated by the transmitter 50 and the antenna 60 depicted in FIG. 1. The RF current in the external antenna may be a pulsed alternating current (AC) or a pulsed DC current, and thus the current induced through the receiver coil 122 would likewise be an AC or pulsed DC current. The current induced in coil 122 may be proportional to the time rate of change of the magnetic field generated at the site of coil 122 by the external RF current source. In some embodiments, a four-diode bridge rectifier 123 may connected across the receiver coil 122 to rectify the AC or pulsed DC current that is induced in the receiver coil 122. A three-position switch device 124 may be connected so that when the switch device 124 is in a first position, the rectifier 123 produces a rectified output that is imposed across a capacitor 125. As such, when the switch device 124 is in the position 1 (as is the case in FIG. 4), the capacitor 125 stores the induced electrical energy.

The switch device 124, in this example, is a voltage-controlled device and is connected to sense a voltage across the capacitor 125 to determine when the capacitor 125 has been sufficiently charged to a specified pacing threshold voltage level. When the capacitor 125 is sensed to have reached the specified pacing threshold level, the voltage-controlled switch device 124 moves to a position 2, which disconnects the capacitor 125 from the coil 122. With the switch device 124 in the position 2, the capacitor 125 is electrically isolated and remains charged, and thus is ready to be discharged. The voltage controlled switch device 124 may comprise a solid state switch, such as a field effect transistor, with its gate connected to the output of a voltage comparator that compares the voltage on capacitor 125 to a reference voltage. The reference voltage may be set at the factory, or adjusted remotely (e.g., after being implanted) via signals sent from the physician programmer unit 70 (FIG. 1), received by coil 122 and processed by circuitry not shown in FIG. 3. Any electronic circuitry contained within the wireless electrode assembly 120, including the voltage controlled switch, can be constructed with components that consume very little power, for example CMOS. Power for such circuitry is either taken from a micro-battery contained within the wireless electrode assembly, or supplied by draining a small amount of charge from capacitor 125.

Still referring to FIG. 3, a narrow band pass filter device 126 may also be connected across the receiver coil 122, as well as being connected to the three-position switch device 124. The band pass filter device 126 passes only a single frequency or communication signal that is induced in the coil 122. The single frequency of the communication signal that is passed by the filter device 126 may be unique for the particular wireless electrode assembly 120 as compared to other implanted wireless electrode assemblies. When the receiver coil 122 receives a short magnetic field burst at this particular frequency, the filter device 126 passes the voltage to the switch device 124, which in turn moves to a position 3.

With the switch device 124 in the position 3, the capacitor 125 may be connected in series through two bipolar electrodes 121 and 129, to the tissue to be stimulated. As such, at least some of the charge that is stored on the capacitor 125 is discharged through the tissue. When this happens, the tissue becomes electrically depolarized. In one example embodiment described in more detail below, the bipolar electrodes 121 and 129 across which stimulation pulses are provided are physically located at opposite ends (e.g., a proximal end and a distal end) of the wireless electrode assembly 120. After a predetermined, or programmed, period of time, the switch returns to position 1 so the capacitor 125 may be charged back up to the selected threshold level.

It should be noted that, for sake of clarity, the schematic diagram of FIG. 3 shows only the electrical components for energy storage and switching for particular embodiments of the wireless electrode assembly 120. Not necessarily shown are electronics to condition the pacing pulse delivered to the tissues, which circuitry should be understood from the description herein. Some aspects of the pulse, for example pulse width and amplitude, may be remotely programmable via encoded signals received through the filter device 126 of the wireless electrode assembly 120. In this regard, filter 126 may be a simple band pass filter with a frequency unique to a particular wireless electrode assembly, and the incoming signal may be modulated with programming information. Alternatively, filter 126 may consist of any type of demodulator or decoder that receives analog or digital information induced by the external source in coil 122. The received information may contain a code unique to each wireless electrode assembly to command discharge of capacitor 125, along with more elaborate instructions controlling discharge parameters such as threshold voltage for firing, duration and shape of the discharge pulse, etc.

Using wireless electrode assemblies of the type shown in FIG. 3, all of the implanted wireless electrode assemblies 120 may be charged simultaneously by a single burst of an RF charging field from a transmitter antenna 60. Because back reaction of the wireless electrode assemblies 120 on the antenna 60 may be small, transmitter 50 (FIG. 1) losses may be primarily due to Ohmic heating of the transmit antenna 60 during the transmit burst, Ohmic heating of the receive coil 122, and Ohmic heating of conductive body tissues by eddy currents induced in these tissues by the applied RF magnetic field. By way of comparison, if eight wireless electrode assemblies 120 are implanted and each is addressed independently for charging, the transmitter 50 may be turned ON eight times as long, which may require almost eight times more transmit energy, the additional energy being primarily lost in heating of the transmit antenna 60 and conductive body tissues. With the wireless electrode assembly 120 of FIG. 3, however, all implanted wireless electrode assemblies can be charged simultaneously with a burst of RF current in antenna 60, and antenna and body tissue heating occurs only during the time required for this single short burst. Each wireless electrode assembly is addressed independently through its filter device 126 to trigger pacing. The transmitted trigger fields can be of much smaller amplitude, and therefore lose much less energy to Ohmic heating, than the transmitted charging pulse.

Pending U.S. patent application Ser. No. 10/971,550 (filed on Oct. 20, 2004), Ser. No. 11/075,375 (filed on Mar. 7, 2005), and Ser. No. 11/075,376 (filed on Mar. 7, 2005), all owned by the assignee of this application, describe various features of wireless electrode assemblies, systems to deliver the wireless electrode assemblies to the heart, and electronic components to activate the wireless electrode assemblies to deliver electrical stimulation. It should be understood from the description herein that some of the features described in these three patent applications (Ser. Nos. 10/971,550, 11/075,375, and 11/075,376) may be applicable to particular embodiments described herein.

Figure 4:
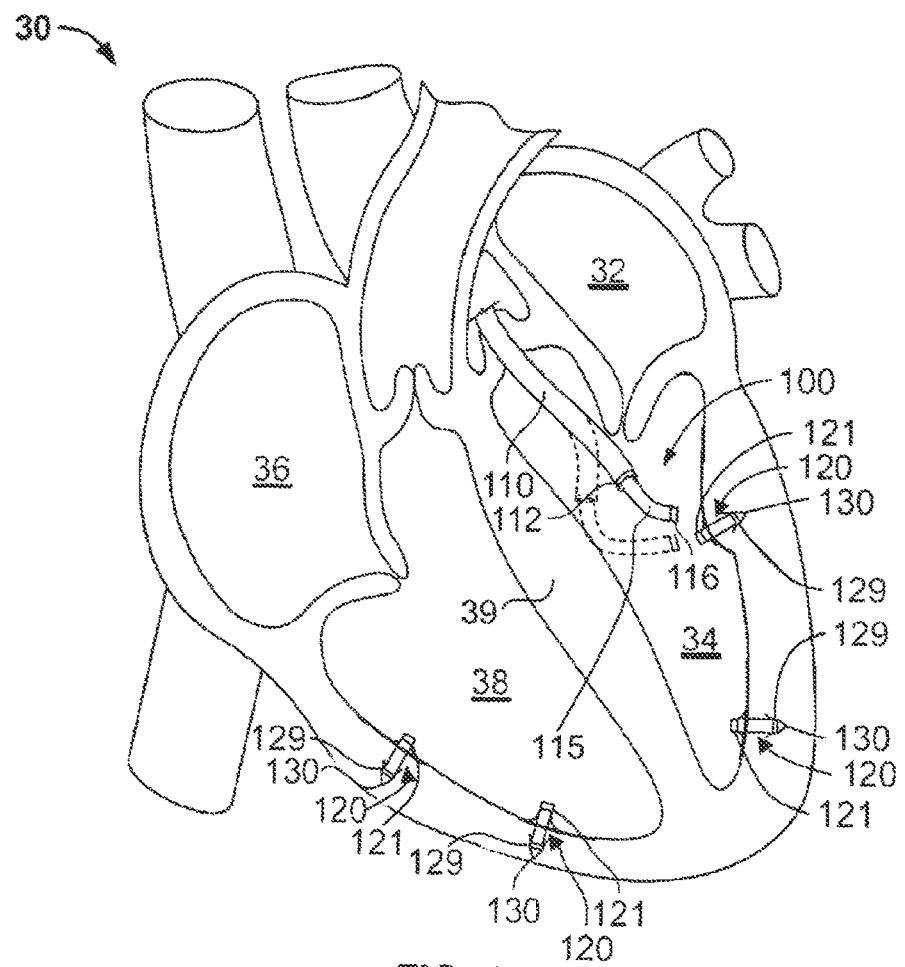
FIG. 4 is a section view of a heart and at least a portion of the electrode delivery system of FIG. 1.

Referring now to FIG. 4, some embodiments of an electrode delivery system 100 may include a guide catheter 110 and a delivery catheter 115. The catheters 110 and 115 may comprise an elongate body that extends from a proximal end (outside the patient's body, not shown in FIG. 4) to a distal end (depicted in FIG. 4 as extending into the patient's heart 30). The delivery catheter 115 fits within a lumen of the guide catheter 110, and can be advanced through the guide catheter 110 so that a distal end of the delivery catheter 115 extends out of a distal opening of the guide catheter 110. The guide catheter 110 may be directed through one or more veins or arteries to the targeted chamber of the heart (e.g., the left ventricle 34 is the targeted chamber in the embodiment shown in FIG. 4). The guide catheter 110 may comprise a steering mechanism (e.g., steering wires, shape memory device, or the like) to shift the distal end and may include at least one marker band 112 to permit viewability of the distal end of the guide catheter 110 using medical imaging techniques. Such a marker band 112 may aid a physician when steering the guide catheter 110 to the targeted heart chamber.

After the guide catheter 110 is deployed into the targeted heart chamber, the wireless electrode assemblies 120 may be advanced into the heart tissue through the guide catheter 110 using at least one delivery catheter 115. The wireless electrode assemblies 120 may be consecutively delivered through the guide catheter 110 using at least one delivery catheter 115. In some embodiments, the delivery catheter 115 may include at least one marker band 116 to permit viewability of the distal end of the delivery catheter 115 using medical imaging techniques. The delivery catheter 115 may include a steering mechanism (e.g., steering wires, shape memory device, or the like) to shift the distal end. For example, the delivery catheter 115 may comprise a shape memory device (e.g., one or more wires comprising Nitinol or another shape memory material) to provide a predetermined curvature near the distal end of the delivery catheter 115. The shape memory device may be activated by a change in electrical charge or by a change in temperature. In one example, the delivery catheter 115 may include a shape memory device near the distal end that is capable of providing a 90-degree deflection curve near the distal end immediately before a longitudinally straight section at the distal end of the catheter 115.

In some approaches to the targeted tissue, the steering mechanism (e.g., steering wires, shape memory device, or the like) of the delivery catheter 115 can be manipulated so that a deflected portion near the distal end of the delivery catheter abuts against the septum wall of the targeted heart chamber. For example, the deflected portion of the delivery catheter may abut against the septum wall 39 between the left ventricle 34 and the right ventricle 38 while a longitudinally straight section of the catheter 115 extends the distal end against the targeted heart chamber wall to receive the wireless electrode assembly 120 (refer to the dotted-line example depicted in FIG. 4). Accordingly, the deflected portion of the delivery catheter 115 can abut against the septum wall to support the position of the distal end of the delivery catheter 115 during the deployment of the wireless electrode assembly 120 into the targeted heart tissue 35 (refer, for example, To FIGS. 7A-D and 8). Such an approach may provide leverage and stability during the insertion process for the electrode assembly 120.

The delivery catheter 115 includes an opening at the distal end in which an associated wireless electrode assembly 120 is retained in a loaded position. The wireless electrode assembly 120 may include a body portion that has a length and a radius configured to be retained with the delivery catheter 115. As described in more detail below, some embodiments of the body portion of the wireless electrode assembly 120 may have a radius, for example, of about 1.25 mm or less and may have a length, for example, of about 10 mm or less. Wireless electrode assemblies configured for insertion into an atrial wall may be smaller than those configured for insertion into the ventricle walls.

In the exemplary embodiment shown in FIG. 4, the wireless electrode assemblies 120 comprise a pointed-tip cylindrical body having a forward portion embedded within the heart wall tissue and a rearward portion that is inside the heart chamber but not fully embedded in the heart wall tissue. The pointed distal tip 130 of the electrode assembly 120 facilitates penetration into the heart wall tissue, and the proximal end of the electrode assembly is configured to remain outside of the heart wall. However, in some embodiments, both the distal tip 130 and the proximal end of the electrode assembly 120 can be embedded within the heart wall tissue 30. As described in more detail below, the electrode assembly 120 may include two fixation devices 132 and 134 that generally oppose one another, such as a set of distal tines and a set of proximal tines. The distal tines can be coupled to and extend from a periphery of a forward portion of the body of the electrode assembly 120, and the proximal tines can be coupled to and extend from a periphery of a rearward portion of the body. As described in more detail below, the set of distal tines extend somewhat outwardly from the body of the electrode assembly 120 but also rearwardly so as to prevent the electrode from becoming dislodged from the heart wall once the electrode assembly 120 is implanted. Also, as described in more detail below, the set of proximal tines extend somewhat outwardly from the body of the electrode assembly 120 but also forwardly so as to prevent the electrode assembly 120 from penetrating entirely through the heart wall.

As the wireless electrode assembly 120 is deployed from delivery catheter 115, tines 132 and 134 located externally on the wireless electrode assembly 120 may adjust to a deployed position (e.g., an outwardly extended condition). Such an adjustment to the deployed position may be caused, for example, due to spring bias of the tines 132 and 134

(described in more detail below). When the tines 132 and 134 are in the deployed position, the tines 132 and 134 are capable of securing the wireless electrode assembly 120 to the targeted tissue site (e.g., described in more detail below, for example, in connection with FIGS. 7-8). In some embodiments, the opening at the distal end of the delivery catheter 115 may be part of conduit that extends through the elongated body of the catheter 115. In other embodiments, the opening at the distal end of the delivery catheter 115 may extend only a partial length into the delivery catheter 115 (e.g., with a narrower channel extending fully to the proximal end of the delivery catheter 115 to provide space for the plunger mechanism 140).

Figure 6:
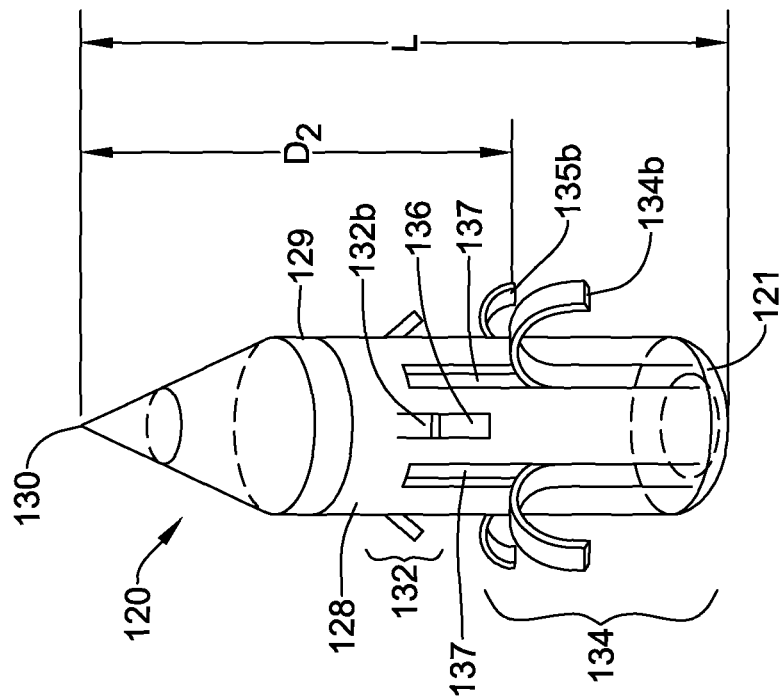
FIG. 6 is a perspective view of a wireless electrode assembly, in accordance with some embodiments of the invention.
Figure 5:
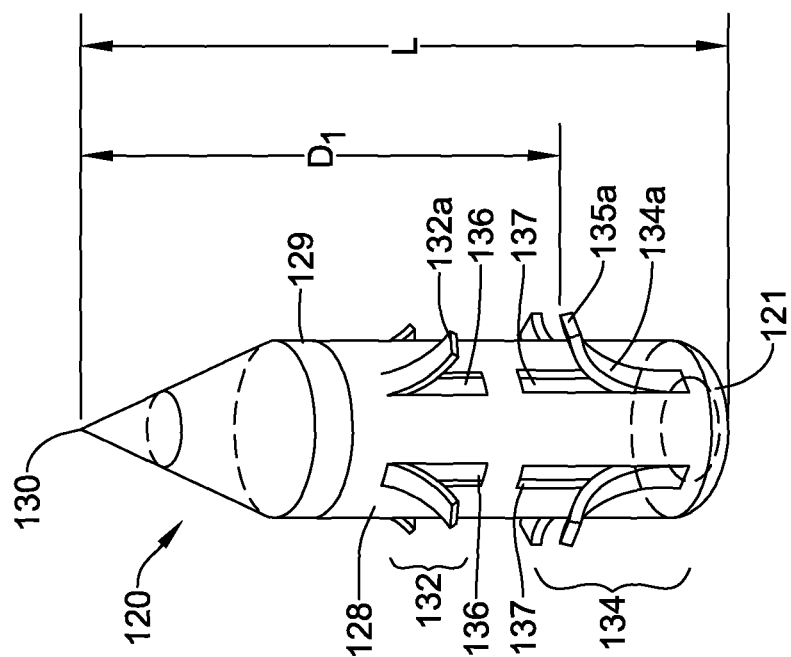
FIG. 5 is a perspective view of a wireless electrode assembly, in accordance with some embodiments of the invention.

Referring to FIGS. 5 and 6, the tines 132 and 134 of the wireless electrode assembly 120 may be configured in a number of orientations. For example, the tines 132 and 134 can be arranged in a configuration (refer to FIG. 5) that permits the electrode assembly 120 to penetrate a substantial length into the heart wall tissue (described in more detail below in connection with FIGS. 7A-7D). In another example, the tines 132 and 134 can be arranged in a configuration (refer to FIG. 6) that permits the electrode assembly 120 to penetrate a lesser amount into the heart wall tissue (described in more detail below in connection with FIG. 8). In some embodiments, wireless electrode assembly 120 may include a proximal electrode 121 at or near a proximal end and a distal electrode 129 at or near a distal end. The proximal electrode 121 and distal electrode 129 may provide bipolar electrode capabilities for the wireless electrode assembly 120, thereby permitting the assembly 120 to supply an electrical charge between the proximal and distal electrodes 121 and 129 (and across the nearby heart tissue).

As previously described, the fixation device 132 may include a set of biased tines arranged near the distal end of the wireless electrode assembly 120 so as to secure the wireless electrode assembly 120 to the heart chamber wall. The fixation device 134 may include a first set of biased tines arranged near the proximal end of the wireless electrode assembly 120 which can also serve to secure the assembly 120 to the heart chamber wall. In some embodiments, the tines 134 arranged near the proximal end may have a different configuration and orientation from the opposing tines 132 arranged near the distal end. For example, as shown in the embodiments depicted in FIGS. 5-6, the distal tines 132 may generally oppose the proximal tines 134. In these circumstances, at least some of the tines 132 and 134 are biased to adjust from a loaded condition to a deployed condition. For example, when in the loaded condition, the tines 132 and 134 may be arranged generally along the body 128 of the wireless electrode assembly 120, within a plurality of recesses 136 and 137, respectively, extending longitudinally along an outer surface of the body 128, so as to fit within the cavity at the distal end of the delivery catheter 115 (refer, for example, to FIG. 7A). When the biased tines 134 and 134 are flexed into the loaded condition, the recesses 136 and 137 receive the tines 132 and 134 to facilitate slidable engagement between the wireless electrode assembly 120 and the delivery catheter 115. The tines 132 and 134 may be biased to adjust to the deployed condition while advancing from the delivery catheter 115. When in the deployed condition, the distal tines 132 may be disposed in an outwardly extended orientation that opposes the outwardly extended orientation of the proximal tines 134. In one example, the distal tip 130 may penetrate into the heart chamber wall when a force is applied to the wireless electrode assembly 120 (e.g., penetrate the endocardium and possibly into the myocardium). During penetration, the tines 132 and 134 are biased to transition from the loaded condition (described in more detail below in connection with FIGS. 7A-D) to the deployed condition as illustrated by tines 132a and 134a (in FIG. 5) and tines 132b and 134b (in FIG. 6). Such a configuration permits the wireless electrode assembly 120 to be readily secured to the heart chamber wall after advancing from the delivery catheter 115.

As previously described, the wireless electrode assembly 120 may be arranged in the delivery catheter 115 (FIG. 4) so that the tines 132 and 134 are in a loaded condition. Thus, when the electrode assembly 120 is advanced out of the distal end of the delivery catheter 115, the tines 132 and 134 transition into their respective deployed conditions. In some embodiments, the tines 132 and 134 may comprise biocompatible material that is capable of flexing from the loaded condition to the deployed condition. For example, one or more of the tines 132 and 134 may comprise a shape memory alloy (e.g., Nitinol or the like), stainless steel, titanium, metal alloys (e.g., nickel-cobalt base alloys such as MP35N), composite materials, or the like.

In the embodiment depicted in FIG. 5, the distal tines 132a and proximal tines 134a can be arranged so that a substantial length of the electrode assemble 120 penetrates into the heart wall tissue. In these circumstances, the distal tines 132a may penetrate in the heart wall tissue to hinder rearward migration of the electrode assembly 120 back into the hear chamber, and the proximal tines 134a are configured to abut or partially penetrate into the wall surface to hinder forward migration of the assembly 120 toward the outside of the heart. Thus, when in the deployed condition, the distal tines 132a oppose migration of the wireless electrode assembly 120 in the generally proximal direction and the proximal tines 134a oppose migration in the generally distal direction. Accordingly, the opposing orientation of the tines 132a and 134a secures the wireless electrode assembly 120 to the heart tissue in a manner so that a portion of the proximal end of the wireless electrode assembly 120 is not embedded in the heart tissue. Because tines 132a and 134a can retain the electrode assembly 120 in the heart tissue without substantial migration, the proximal end of the electrode assembly body 128 can be incorporated into the surrounding heart tissue over a period of days or weeks. In these embodiments, the wireless electrode assembly 120 may be immobilized by the surrounding tissue to prevent future dislodgement. In such circumstances, the patient may receive anti-coagulants, Aspirin, or other drugs (e.g., PLAVIX, CUMODIN, etc.) for several months after the operation or until incorporation of the wireless electrode assembly 120 into the surrounding tissue has occurred.

In this embodiment depicted in FIG. 5, the distal tines 132a and the proximal tines 134a are slightly curved and are oriented in an opposing manner when in the deployed condition. The curvature of the proximal tines 132 is such that the tines 134a contact the surface of the heart tissue near the proximal tines' extremities. In addition, the proximal tines 134a can be positioned along the body 128 and curved in a manner so that the free end 135a of each proximal tine 134a abuts or partially penetrates into the heart wall tissue after a portion of the electrode assembly 120 has penetrated therein. The wireless electrode assembly 120 can be advanced into the heart wall tissue 35 so that the proximal tines 134a cause a slight spring-back action after abutting or partially penetrating into the heart wall tissue. For example, the proximal tines 134a may flex outwardly when forced into engagement with the heart wall tissue, and such an outward flexing action can cause a slight spring back motion to the wireless electrode assembly 120. The distal tines 132a may flex outwardly in response to this slight spring-back motion in the proximal direction, thereby enhancing the engagement of the heart tissue between the distal tines 132a and the proximal tines 134a.

Still referring to FIG. 5, the proximal tines 134a can be positioned along the body 128 and curved in a manner so that the free end 135a of each proximal tine 134a abuts or partially penetrates into the heart wall tissue after a substantial portion of the electrode assembly 120 has penetrated therein. For example, in this embodiment, the proximal tines 134a are configured such that the free end 135a of each tine 134a (when in the deployed condition) is disposed a longitudinal distance $D_1$ rearward of the distal tip 130. In this embodiment, the longitudinal distance $D_1$ is greater than half the overall length L of the electrode assembly 120. In such circumstances, a majority of the length of the electrode assembly 120 can penetrate into the heart wall tissue before the proximal tines 134a engage the heart wall to oppose forward migration. This example of substantial penetration of the electrode assembly 120 into the heart wall tissue may be effective when advancing the electrode assembly 120 into portions of the heart having thicker myocardial walls (e.g., some heart walls around the left and right ventricles). In addition, when a substantial portion of the electrode assembly 120 penetrates into the heart tissue, the non-penetrating proximal portion of the electrode assembly 120 is reduced, thereby promoting efficient healing and incorporation into the surrounding heart tissue.

In the embodiment depicted in FIG. 6, the distal tines 132b and proximal tines 134b can be arranged so that a lesser length of the electrode assembly 120 penetrates into the heart wall tissue. For example, the distal tines 132b may be substantially different in length than the proximal tines 134b. Also, the proximal tines 134b may have a greater curvature than the proximal tines 134a previously described in connection with FIG. 5 so that the contact between the surface of the heart tissue and the proximal tines is near the apex of the curvature. In these embodiments, the proximal tines 134b can be positioned along the body 128 and curved in a manner so that the curvature apex 135b of each proximal tine 134b abuts the heart wall tissue after a partial length of the electrode assembly 120 has penetrated therein. For example, the proximal tines 134b are configured such that the apex 135b (when in the deployed condition) is disposed at a longitudinal distance $D_2$ rearward of the distal tip 130. In this embodiment, the longitudinal distance $D_2$ is about half the overall length L of the electrode assembly 120. Accordingly, about half of the electrode assembly 120 can penetrate into the tissue before the proximal tines 134b oppose forward migration. Such penetration to a limited length of the electrode assembly 120 may be effective when advancing the electrode assembly 120 into portions of the heart wall having a reduced wall thickness (e.g., some heart walls around the right atrium).

As previously described, the tines 132b and 134b are oriented in an opposing fashion to secure the wireless electrode assembly 120 to the heart tissue in a manner that opposes reward migration and forward migration, thereby permitting incorporation into the surrounding tissue. For example, the proximal tines 134b may flex outwardly when forced against the heart wall tissue, and such an outward flexing action can cause a slight spring back motion to the wireless electrode assembly 120. The distal tines 132b may flex outwardly in response to this slight spring-back motion in the proximal direction, thereby enhancing the engagement of the heart tissue between the distal tines 132b and the proximal tines 134b.

In some embodiments, the proximal tines 134b of the electrode assembly may be nonaligned with the distal tines 132b along the body of the electrode assembly 128. For example, as shown in FIG. 6, the distal tines 132b may be tangentially shifted about 45° along the body circumference as compared to the proximal tines 134b so that the proximal tines 134b and distal tines 132b are nonaligned. As described in more detail below in connection with FIG. 8, such nonalignment between the proximal tines 134b and the distal tines 132b can permit one set of tines (e.g., the proximal tines 134b) to partially deploy before fully exiting the distal opening of the delivery catheter 115. In these circumstances, the partial deployment of the proximal tines 134b before fully exiting the delivery catheter 115 can facilitate the abutting engagement between the proximal tines 134b and the heart chamber wall.

It should be understood that in some embodiments of the wireless electrode assembly 120, the distal tines 132 may also serve as at least a portion of the distal electrode 129. Also, in some embodiments, proximal tines 134 may also serve as at least a portion of the proximal electrode 121. For example, the tines 132 and 134 may comprise an electrically conductive material (e.g., stainless steel or another metallic material) and may be electrically connected to the distal and proximal electrode circuitry (respectively).

Referring now to FIGS. 7A-D, some embodiments of the wireless electrode assemblies 120 may be press fit into the conduit of the delivery catheter 115 so that a plunger mechanism 144 may be used to separate the wireless electrode assembly 120 from the delivery catheter 115. As shown in FIG. 7A, the delivery catheter 115 may be steered and directed toward a targeted site at the surface of heart tissue 35 (e.g., a heart chamber wall). The delivery catheter 115 may contain at least a distal portion of a tube portion 142 that is coupled to an actuation rod 140. As previously described, in some approaches to the targeted tissue, the steering mechanism (e.g., steering wires, shape memory device, or the like) of the delivery catheter 115 can be manipulated so that a deflected portion near the distal end of the delivery catheter 115 abuts against the septum wall of the targeted heart chamber. For example, the portion 117 (FIG. 7A) of the delivery catheter 115 may be deflected to abut against the septum wall while a longitudinally straight section of the catheter 115 extends toward the targeted heart tissue 35. As such, some portion (e.g., portion 117) the delivery catheter 115 can abut against the septum wall to support the position of the distal end of the delivery catheter 115.

The wireless electrode assembly 120 may be releasably engaged with the tube portion 142. For example, the wireless electrode assembly 120 may be press-fit into the tube portion 142. In another example, the tube portion 142 may have a square cross-sectional shape, a hexagonal cross-sectional shape, a keyed cross-sectional shape, or other noncircular cross-sectional shape to engage the complementary shaped body of the wireless electrode assembly 120. The tube portion 140 may be substantially rigid so as to retain the fixation devices 132 and 134 of the wireless electrode assembly 120 in a loaded condition (as shown, for example, in FIG. 7A). In some embodiments, one or both of the actuation rod 140 and the plunger mechanism 144 may extend to an actuation device (e.g., a hand-operated trigger mechanism) at the proximal end of the delivery catheter 115 outside the patient's body. In some embodiments, the tube portion 142 and the actuation rod 140 may be fixedly arranged in the delivery catheter 115 so as to deliver one electrode assembly at a time. Alternatively, the tube portion 142 and the actuation rod 140 may be movable through lumen of the delivery catheter 115 so that a number of electrode assemblies can be consecutively passed through the delivery catheter 115.

As shown in FIG. 7B, the distal end of the delivery catheter 115 may about the surface of the heart tissue 35 to prepare the wireless electrode assembly 120 for fixation to the tissue 35. In this embodiment, the distal end of the delivery catheter 115 includes a marker band 116 to facilitate the steering and guidance of the delivery catheter (e.g., a physician may employ medical imaging techniques to view the marker band 116 while the delivery catheter 115 is in the heart 30).

Referring to FIG. 7C, the electrode assembly 120 can be advanced through the distal opening of the delivery catheter 115 (and the tube portion 142) and into the tissue 35. This operation may be performed by advancing the plunger mechanism 144 against the proximal end of the wireless electrode assembly 120 to thereby force the distal tip 130 of the wireless electrode assembly 120 to penetrate through the endocardium and possibly into the myocardium. For example, the force may be applied by manipulating the actuation device (e.g., the hand-operated trigger mechanism connected to the proximal end of the plunger mechanism 144) to force the plunger mechanism 144 in the distal direction relative to the actuation rod 140 (and the tube portion 142). As such, the distal tip 130 of the electrode assembly 120 pierces the tissue surface and advances into the tissue 35.

Referring to FIG. 7D, when the delivery catheter 115 is fully separated from the wireless electrode assembly 120, the fixation devices 132 and 134 can transition from a loaded condition to a deployed condition. In this embodiment, the fixation devices 132 and 134 comprise tines that are biased to the deployed condition (refer, for example, to FIGS. 5-6) after being released from the tube portion 142 of the delivery catheter 115. As previously described in connection with FIG. 5, the tines 132 and 134 can be configured so that a substantial portion of the electrode assembly 120 penetrates into the tissue 35 before the forward migration is hindered by the proximal tines 134. For example, the electrode assembly 120 can penetrate the longitudinal length $D_1$ into the heart tissue 35 so that a majority of the overall length of the electrode assembly 120 is advanced into the tissue 35. In these embodiments, the distal tines 132a can transition to the deployed condition in which each tine 132a is outwardly extended in a generally proximal direction when the distal tip 130 penetrates into the heart tissue 35. Also, in these embodiments, the proximal tines 134a can transition to the deployed condition in which each tine 134a is extended outwardly in a generally distal direction when the delivery catheter 115 is separated from the proximal end of the wireless electrode assembly 120. The proximal tines 134a have a base 150 affixed to the body of electrode assembly 120.

As previously described, in some circumstances, the proximal tines 134a may flex outwardly when forced against the heart wall tissue, and such an outward flexing action can cause a slight spring back motion to the wireless electrode assembly 120. The distal tines 132a may flex outwardly in response to this slight spring-back motion in the proximal direction, thereby enhancing the engagement of the heart tissue 35 between the distal tines 132a and the proximal tines 134a. Such an opposed orientation of the tines 132a and 134a hinders rearward migration and forward migration of the electrode assembly 120. As previously described, the tissue 35 may grow and eventually incorporate the wireless electrode assembly 120 therein, thereby preventing the wireless electrode assembly 120 from dislodgement from the tissue 35. In the example depicted in FIG. 7D, the proximal tines 134a are illustrated as abutting against the heart tissue 35. It should be understood that, in some embodiments, the proximal tines 134a may at least partially penetrate into the heart tissue 35 when the electrode assembly 120 is advanced therein.

Referring to FIG. 8, other embodiments of the wireless electrode assembly 120 include fixation devices 132 and 134 that transition into different configurations. For example, the fixation devices 132b and 134b may include tines that are biased to transition into a deployed condition (after being released from the delivery catheter 115) as described in connection with FIG. 6. In such embodiments the tines 132b and 134b may deploy to outwardly extended orientations that generally oppose one another. The tines 132 and 134 can be configured so that a limited length of the electrode assembly 120 penetrates the tissue 35 before the forward migration is opposed by the proximal tines 134b (e.g., before the curvature apex 135b abuts the tissue 35). For example, the electrode assembly 120 can penetrate the longitudinal length $D_2$ into the heart tissue 35 so that about half of the overall length of the electrode assembly 120 is advanced into the tissue 35. As previously described, in some circumstances, the proximal tines 134b may flex outwardly when forced against the heart wall tissue 35, and such an outward flexing action can cause a slight spring back motion to the wireless electrode assembly 120. The distal tines 132b may flex outwardly in response to this slight spring-back motion in the proximal direction, thereby enhancing the engagement of the heart tissue 35 between the distal tines 132b and the proximal tines 134b. Such opposed orientations of the tines 132b and 134b hinders rearward and forward migration of the electrode assembly 120. Also, as previously described, the tissue 35 may grow and eventually incorporate the wireless electrode assembly 120 therein, thereby preventing the wireless electrode assembly 120 from dislodgement from the tissue 35.

Still referring to FIG. 8, the proximal tines 134b may be configured to at least partially deploy before exiting the distal opening of the delivery catheter 115. As such, the proximal tines 134b may at least partially curve outwardly from the body 128 of the electrode assembly before contacting the heart wall tissue 35. In these circumstances, the proximal tines 134b may curve so as to abut against the heart wall tissue 134b without the extremities of the proximal tines 134b penetrating into the tissue 35. Because the proximal tines 134b can at least partially deploy before exiting the distal opening of the delivery catheter 115, the proximal tines 134b can achieve the greater curvature previously described in connection with FIG. 6 so that the contact between the heart tissue 35 and the proximal tines 134b is near the curvature apex 135b (FIG. 6).

For example, in some embodiments, electrode assembly 120 can be arranged in the tube portion 142 so that the proximal tines 134b are aligned with deployment slots 146 (FIG. 8) formed in the tube portion 142. Accordingly, when the electrode assembly is advanced into the heart tissue 35, the proximal tines 134b at least partially extend outwardly into the deployment slots 146, thereby permitting the proximal tines 134b to partially deploy before exiting the distal opening of the delivery catheter 115. As previously described in connection with FIG. 6, the proximal tines 134b may be nonaligned with the distal tines 132b along the body of the electrode assembly 128. Such nonalignment between the proximal tines 134b and the distal tines 132b can permit the proximal tines 134b to partially deploy in the deployment slots 146 while the distal tines 132b are retained against the electrode body 128 in the tube portion 142. Alternatively, the distal tines 132b can be generally aligned with the proximal tines 134b so that both the distal tines 132b and the proximal tines 134b pass through the deployment slots 146 during advancement of the electrode assembly 120 from the delivery catheter 115. It should be understood that, in some embodiments, the deployment slots 146 may extend through the distal circumferential end of the delivery catheter 115 so that the proximal tines 134b can at least partially deploy through the distal circumferential end of the delivery catheter 115 before exiting the distal opening of the delivery catheter 115.

In some embodiments of the delivery catheter 115 described herein, the delivery catheter 115 may be wholly separate from the actuation rod 140 so that the actuation rod 140 slides through a conduit passing through the delivery catheter 115. In such circumstances, the actuation rod 140 may be completely retracted from the delivery catheter so that a second wireless electrode assembly may be detachably coupled to the actuation rod 140 (or to an unused, different actuation rod 140) and then directed through the delivery catheter 115 already disposed in the patient's body. In other embodiments, the delivery catheter 115 and the actuation rod 140 may be coupled to one another. In such circumstances, the delivery catheter 115 and actuation rod 140 may be removed from the guide catheter 110 (FIG. 4) so that a second wireless electrode assembly may be detachably coupled to the actuation rod 140 (or to a previously unused delivery catheter/actuation rod having a similar construction) and then directed through the guide catheter 110 already disposed in the patient's body.

In some embodiments, the delivery catheter 115 may include a tube portion that is configured to retain a plurality of wireless electrode assemblies 120 (e.g., similar to tube portion 142 but having a greater length to receive a multitude of assemblies 120). For example, the delivery catheter may be configured to carry two, three, four, five, ten, twelve, or more electrode assemblies 120 in a serial (end to end) arrangement. As such, the plunger mechanism 144 can be used to force each electrode assembly 120 into different tissue sites without retracting the delivery catheter out of the heart. As described previously, the actuation mechanism may force the plunger 144 in a generally distal direction. In the serially arranged embodiment, the plunger 144 applies the force to the most rearward assembly 120 in the serial arrangement, which in turn applies a force from the distal tip 130 of the most rearward assembly 120 to the proximal end of the next assembly 120 in the serial arrangement. In this fashion, the application of force can propagate through the serial arrangement until the assembly 120 nearest the heart tissue is delivered to the target site (as described previously, for example, in connection with FIG. 7D). It should be understood that the serial arrangement may comprise electrode assemblies 120 as described in connection with FIG. 5, as described in connection with FIG. 6, or some combination thereof.

Some of the embodiments described herein permit a plurality of pacing electrodes to be deployed at multiple pacing sites. The pacing sites may be located in the left atrium 32, the left ventricle 34, the right atrium 36, the right ventricle, or a combination thereof. Furthermore, the pacing electrodes may comprise wired pacing leads 95 (FIG. 1), wireless electrode assemblies, or a combination thereof. Providing electrical stimulation at multiple pacing sites and in multiple heart chambers may be used to treat a number of conditions. One such condition is congestive heart failure (CHF). It has been found that CHF patients have benefited from hi-ventricular pacing, that is, pacing of both the left ventricle 34 and the right ventricle 38 in a timed relationship. It is believed that many more patients could benefit if multiple sites in the left and right ventricles 34 and 36 could be synchronously paced. In addition, pacing at multiple sites may be beneficial where heart tissue through which electrical energy must propagate is scarred or dysfunctional, which condition halts or alters the propagation of an electrical signal through that heart tissue. In these cases, multiple-site pacing may be useful to restart the propagation of the electrical signal immediately downstream of the dead or sick tissue area. Synchronized pacing at multiple sites on the heart may inhibit the onset of fibrillation resulting from slow or aberrant conduction, thus reducing the need for implanted or external cardiac defibrillators. Arrhythmias may result from slow conduction or enlargement of the heart chamber. In these diseases, a depolarization wave that has taken a long and/or slow path around a heart chamber may return to its starting point after that tissue has had time to re-polarize. In this way, a never ending "race-track" or "circus" wave may exist in one or more chambers that is not synchronized with normal sinus rhythm. Atrial fibrillation, a common and life threatening condition, may often be associated with such conduction abnormalities. Pacing at a sufficient number of sites in one or more heart chambers, for example in the atria, may force all tissue to depolarize in a synchronous manner to prevent the race-track and circus rhythms that lead to fibrillation.

A number of embodiments of the invention have been described. Nevertheless, it will be understood that various modifications may be made without departing from the spirit and scope of the invention. Accordingly, other embodiments are within the scope of the following claims.

What is claimed is:
1. An electrical stimulation system for provide pacing therapy to a heart, the system comprising:
  a pulse generator device including a wired lead extending therefrom; and
  a wireless electrode assembly separate from the pulse generator device, the wireless electrode assembly including:
    a body having a distal end region extending to a distal end of the body and a proximal end region extending to a proximal end of the body;
    a first electrode secured to the distal end of the distal end region of the body;
    a second electrode disposed on the proximal end region of the body; and
    a tissue fixation member configured to engage cardiac tissue to secure the wireless electrode assembly within a chamber of the heart;
    wherein the tissue fixation member comprises a flexible tine including a base, a tip and a medial portion extending therebetween;
    wherein the base of the tine is secured to the body between the first electrode and the second electrode;
    wherein the tine transitions from a straightened delivery configuration to a curved deployed configuration;
  wherein the electrical stimulation system is configured to synchronize electrical stimulation to the heart provided with the wireless electrode assembly to electrical stimulation to the heart provided with the wired lead of the pulse generator.

2. The system of claim 1, wherein the tip of the tine is positioned distal of the base in the straightened delivery configuration.

3. The system of claim 1, wherein both the base of the tine and the first electrode remain immovably fixed to the body while the tine transitions from the straightened delivery configuration to the curved deployed configuration.

4. The system of claim 1, wherein the wireless electrode assembly further includes a circuit positioned within the body, and wherein the circuit is designed to deliver electrical energy to the first electrode.

5. A method of providing pacing therapy to a heart of a patient, comprising:
   implanting a wireless electrode assembly into a chamber of the heart, the wireless electrode assembly including:
     a body having a distal end region extending to a distal end of the body and a proximal end region extending to a proximal end of the body;
     a first electrode secured to the distal end of the distal end region of the body;
     a second electrode disposed on the proximal end region of the body; and
     a tissue fixation member engaging cardiac tissue to secure the wireless electrode assembly within the chamber of the heart, the tissue fixation member comprising a tine including a base, a tip and a medial portion extending therebetween;
   wherein the base is secured to the body between the first electrode and the second electrode;
   wherein the tine transitions from a straightened delivery configuration while the wireless electrode assembly is being advanced to the heart to a curved deployed configuration when the wireless electrode assembly is implanted in the chamber of the heart;
   implanting a wired lead extending from a pulse generator within the patient;
   providing electrical stimulation to the heart with the wireless electrode assembly;
   providing electrical stimulation to the heart with the wired lead of the pulse generator; and
   synchronizing the electrical stimulation to the heart provided with the wireless electrode assembly to the electrical stimulation to the heart provided with the wired lead of the pulse generator.

6. The method of claim 5, wherein the pulse generator wirelessly communicates with a controller implanted in the patient.

7. The method of claim 6, wherein the controller communicates with the wireless electrode assembly.

8. The method of claim 7, wherein the wireless electrode assembly includes a circuit designed to deliver electrical energy provide electrical stimulation to the heart.

9. The method of claim 5, further comprising:
   sensing an ECG signal with the pulse generator.

10. The method of claim 5, wherein the wired lead is implanted in a right atrium or right ventricle of the heart, and the wireless electrode assembly is implanted in a left atrium or left ventricle of the heart.

11. The method of claim 5, further comprising:
   implanting a second wireless electrode assembly into another chamber of the heart.

* * * * *